(12) United States Patent
Goffer

(10) Patent No.: US 7,153,242 B2
(45) Date of Patent: Dec. 26, 2006

(54) GAIT-LOCOMOTOR APPARATUS

(76) Inventor: Amit Goffer, 1, Ha'seifan st., Kiryat Tivon, 36531 (IL)

( * ) Notice: Subject to any disclaimer, the term of this patent is extended or adjusted under 35 U.S.C. 154(b) by 689 days.

(21) Appl. No.: 09/864,845

(22) Filed: May 24, 2001

(65) Prior Publication Data

US 2003/0093021 A1 May 15, 2003

(51) Int. Cl.
*A63B 21/00* (2006.01)
(52) U.S. Cl. ................... 482/66; 482/74; 482/75
(58) Field of Classification Search ............ 482/75, 482/76, 74, 67; 601/33–35; 700/245, 253
See application file for complete search history.

(56) References Cited

U.S. PATENT DOCUMENTS

| 4,206,558 A | * | 6/1980 | Bivona ................ 36/7.5 |
|---|---|---|---|
| 4,422,453 A | | 12/1983 | Salort |
| 4,697,808 A | | 10/1987 | Larson et al. |
| 4,945,616 A | | 8/1990 | Hart |
| 5,081,989 A | | 1/1992 | Graupe et al. |
| 5,112,296 A | | 5/1992 | Beard et al. |
| 5,282,460 A | | 2/1994 | Boldt |
| 5,476,441 A | | 12/1995 | Durfee et al. |
| 5,662,693 A | | 9/1997 | Johnson et al. |
| 5,961,476 A | | 10/1999 | Betto et al. |
| 5,961,541 A | | 10/1999 | Ferrati |
| 6,741,911 B1 | * | 5/2004 | Simmons .............. 700/245 |

FOREIGN PATENT DOCUMENTS

| GB | 2260495 A | 4/1993 |
|---|---|---|
| GB | 2301776 A | 12/1996 |

OTHER PUBLICATIONS

Kralj, A. in "Gait Restoration in Paraplegic Patients: A Feasibility Demonstration Using Multichannel Surface Electrodes FES", J. Rehab. Res. Dev., vol. 20 pp. 3-20 (1983).

IRBY et al. in "Automatic Control Design for a Dynamic Knee Brace System" IEEE Trans. Rehab. Eng., vol. 7, pp. 135-139.

Collins Wisse and Ruina, "A 3-D Passive Dynamic Walking Robot with Two Legs and Knees", Submitted to publication in the International Journal of Robotics Research, Feb. 2001.

Finley, F.R., and Kapovich, P.V., "Electrogoniometric Analysis of Normal and Pathological Gaits," Res. Quart. 1964, pp. 379-384, vol. 35.

Morris, J.R.W., "Accelerometry—A Technique for the Measurements of Human Body Movements," J. Biomech. 1973, pp. 729-736, vol. 6.

* cited by examiner

*Primary Examiner*—Jerome W. Donnelly
(74) *Attorney, Agent, or Firm*—Shalom Wertsberger; Saltamar Innovations

(57) ABSTRACT

The gait-locomotor apparatus of the present invention is a device for overcoming impeded locomotion in humans and is aimed at enabling people with handicapped lower limbs to walk. The gait-locomotor apparatus that is wore on a disabled user comprises a brace having a plurality of jointed segments that are adapted to fit the lower body of the disabled user and propulsion means that is adapted to provide relative movement between the plurality of jointed segments. The gait-locomotor apparatus further comprises at least one sensor adapted to monitor the angular position of at least one of the plurality of jointed segments and a control unit that is adapted to supervise the propulsion means and to receive feedback information from the sensors so as to facilitate the brace to perform walking patterns. The disabled user that wears the gait-locomotor apparatus of the present invention is able to steadily stand in a stance position supported by the brace, and is able to walk in various walking patterns using the control unit while fully participating in the process.

64 Claims, 16 Drawing Sheets

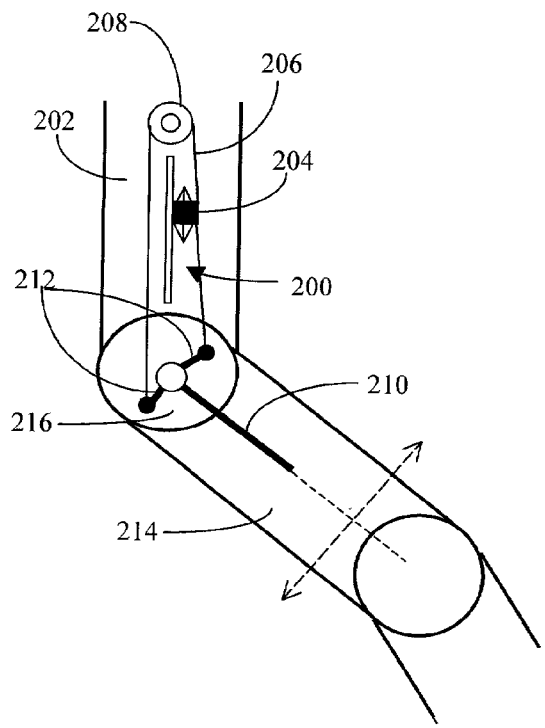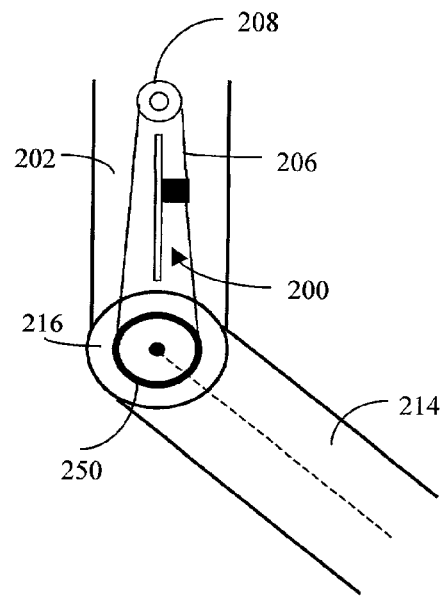
Figure 9a Figure 9b
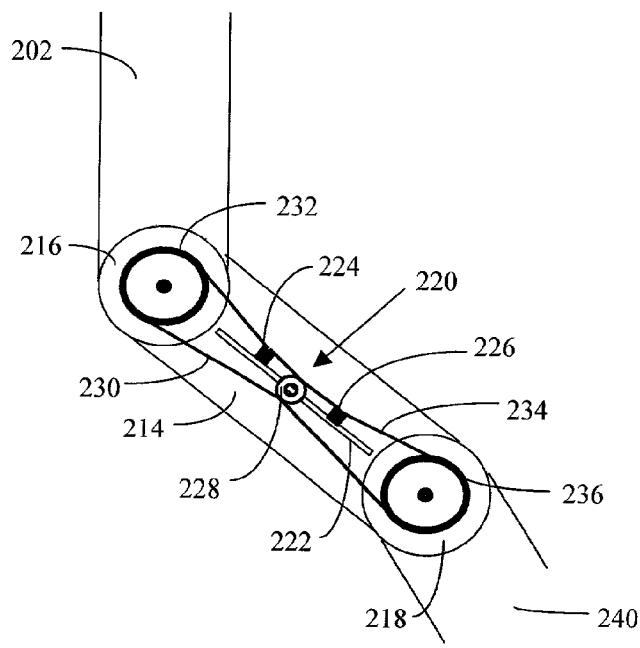
Figure 9c

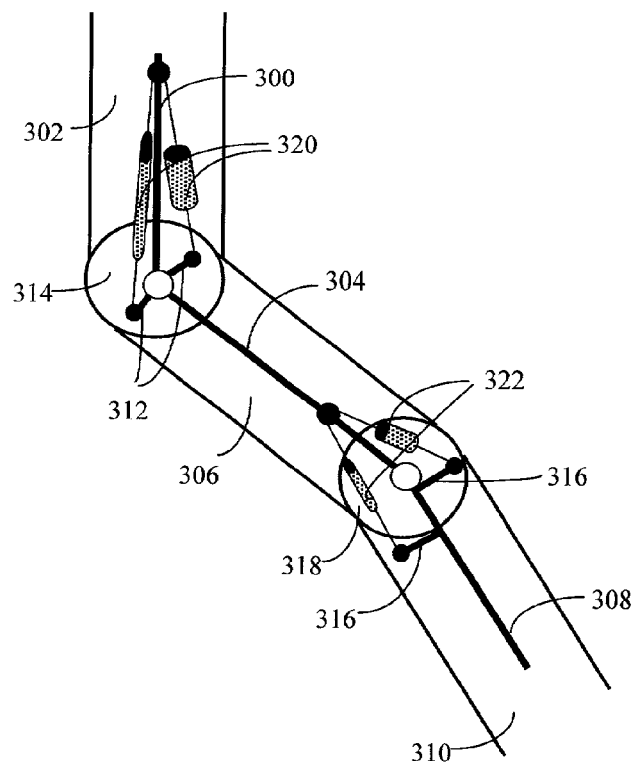
Figure 10
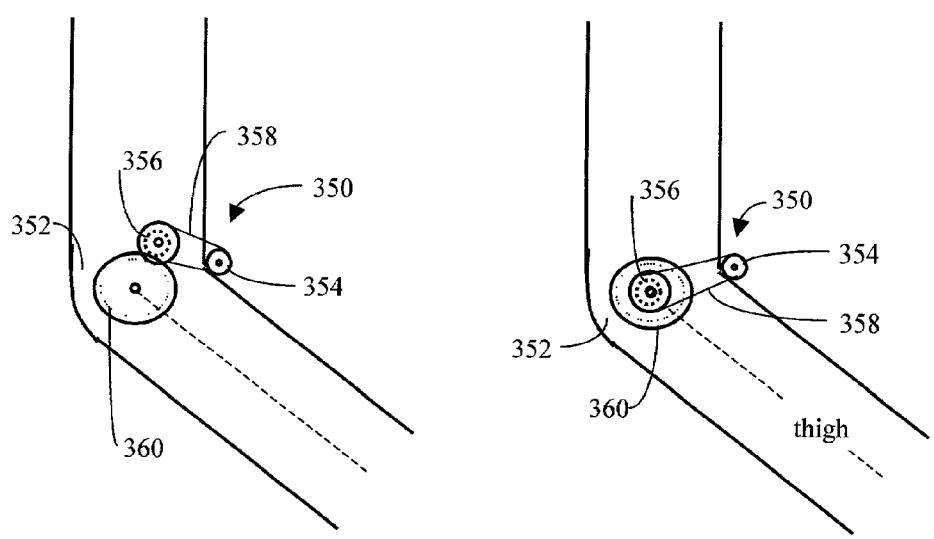
Figure 11aFigure 11b

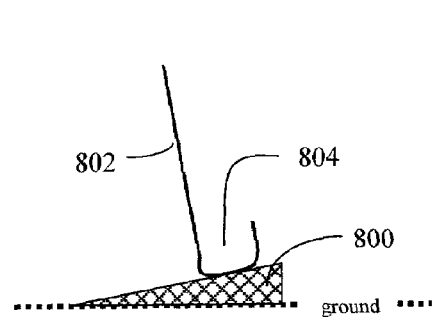
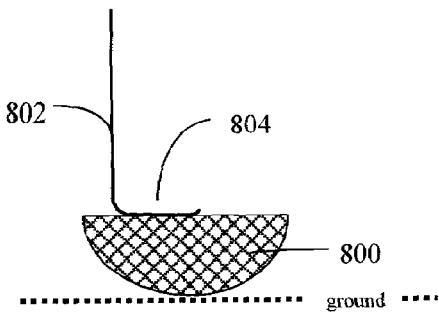
Figure 16a
Figure 16b
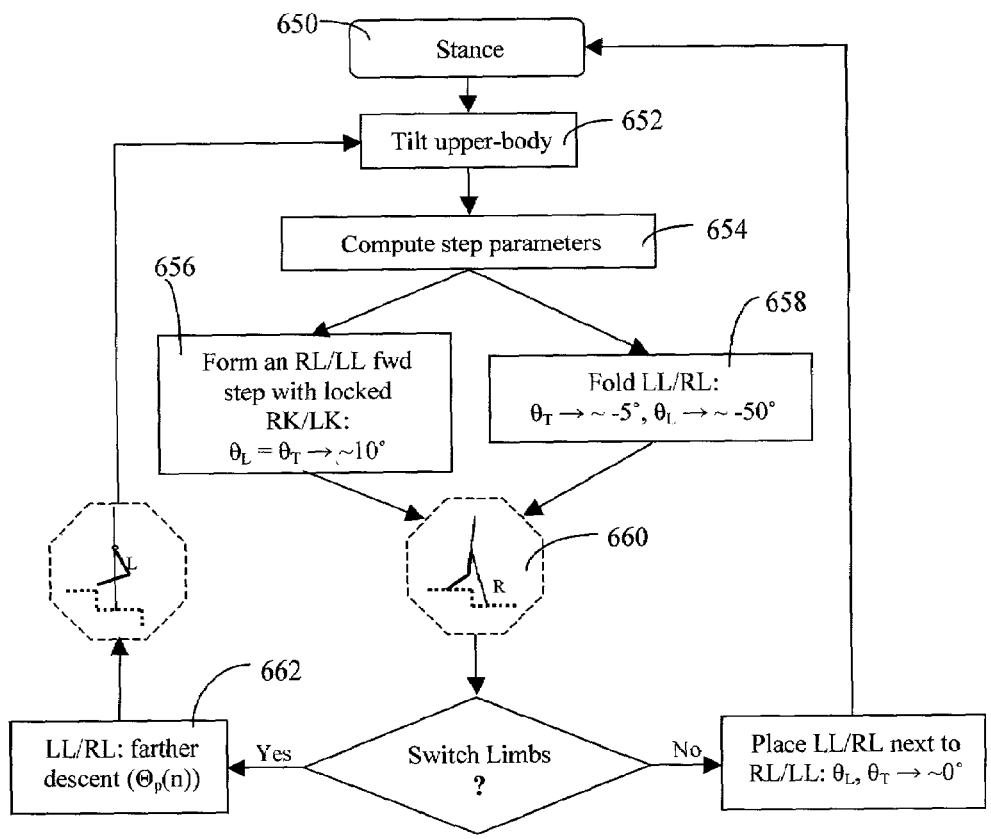
Figure 17

GAIT-LOCOMOTOR APPARATUS

FIELD OF THE INVENTION

The present invention relates to a device and method for walking assistance and locomotion. More particularly, the present invention relates to a device and method for overcoming impeded locomotion disabilities.

BACKGROUND OF THE INVENTION

About 1.6 million people in the USA alone are confined to wheelchairs that serve as their only means of mobility. As a result, their lives are full of endless obstacles such as stairs, rugged pavement and narrow passages. Furthermore, lack in standing position for long periods of time and having only limited upper-body movements, often inflict hazardous health complications. In order to prevent rapid health deterioration, expensive equipment such as standing frames and trainers must be used in addition to ample physio/hydro-therapy.

Functional Electrical Stimulation (FES) is a known method in which electrodes are attached to various bodily parts (legs and thighs) and electrical pulses are applied to the muscles in order to invoke muscles motion and consequently impose a gait. The use of FES is discussed by Kralj, A. in "Gait Restoration in Paraplegic Patients: A Feasibility Demonstration Using Multichannel Surface Electrodes FES", J. Rehab. Res. Dev., vol. 20, pp. 3–20 (1983). In this method, choosing the proper parameters for the pulse sequences (amplitude, shape, frequency and timing) and real-time adapting these parameters along the gait are of the main research areas of that field. While FES is a true muscle-based walking, the main disadvantage of this method is in the fact that it does not provide an effortless usage and an efficient restoration of functional daily activities.

An Example of an approach that addresses the problem of gait restoration is disclosed in U.S. Pat. No. 4,422,453 "External Apparatus for Vertical Stance and Walking for those with Handicapped Motor Systems of the Lower Limbs" by Salort and filed in 1982. In this patent, a corset and girdles are attached to the body. The harness contains strips of flexible metal capable of absorbing and restoring the flexural and torsonal stresses. The locomotive force in this case is bodily based and is actually a reciprocal gait orthosis (RGO), which is a walk-assisting device, that does not provide a practical daily solution to the handicapped person. Other examples of RGO devices are disclosed in U.S. Pat. No. 5,961,476 "Walk Assisting Apparatus" by Betto et al., filed in 1997 and U.S. Pat. No. 4,946,156 by Hart, filed in 1988. The first patent by Betto discloses a walk assisting apparatus that comprises full leg brace for both legs interconnected by links to the coxa so as to provide leg supports to make the alternate walk properly. The later patent by Hart discloses a reciprocation gait orthosis that comprises hip joints coupled to a push/pull member, which is thigh fit, as well as two limb members.

In general, the RGO are non-motorized brace systems that are wore by the user, while the user himself performs the locomotion. Any type from the available RGO is better fitted as a trainer than a functional walking aid.

Motorized bracing system is disclosed in U.S. Pat. No. 5,961,541 "Orthopedic Apparatus for Walking and Rehabilitating Disabled Persons Including Tetraplegic Persons and for Facilitating and Stimulating the Revival of Comatose Patients through the Use of Electronic and Virtual Reality Units" by Farrati, filed in 1998. This patent discloses an exoskeleton for the support of a patient's body that is jointed opposite the hip and knee articulations, and is provided with a number of small actuators that are designed to move jointed parts of the exoskeleton in accordance with the human gait. Though the bracing system is motorized, it is a therapeutic device that is not intended for daily functional locomotive activities. The apparatus is confined along a rail or a conveyor, where the user is not involved in the walking process beyond starting and stopping the gait.

Another locomotion aid, a self-contained electronically controlled dynamic knee-brace system, which aim to add a flexion to knee orthosis is disclosed by Irby et al. in "Automatic Control Design for a Dynamic Knee-Brace System", IEEE Trans. Rehab. Eng., vol. 7, pp. 135–139 (1999).

All the above discussed rehabilitation devices for disabled persons confined to wheelchairs as well as available devices in rehabilitation institutions are used for training purposes only. A solution that enables daily independent activities that restore the dignity of handicapped persons, dramatically ease their lives, extend their life expectancies and reduce medical and other related expenses is so far not available.

SUMMARY OF THE INVENTION

It is an object of the present invention to provide a new and unique gait-locomotor apparatus and method that is a detachable light gait-locomotive orthosis.

It is another object of the present invention to provide a gait-locomotor apparatus in which the user is involved in the gait-restoration process.

It is yet another object of the present invention to provide a gait-locomotor apparatus in which natural and intentional upper-body movements (tilts) are used to initiate and maintain gait as well as determine various parameters without the need to use hands or voice for commanding the device. The device of the present invention offers, for the first time, a practical solution to many of the daily mobility functions.

It is an additional object of the present invention to provide a new and unique method to enable disabled people to walk using a gait-locomotor apparatus.

It is thus provided a gait-locomotor apparatus that is wore on a disabled user, said gait-locomotor apparatus comprising:
  a brace having a plurality of jointed segments, said brace adapted to fit the lower body of the disabled user;
  propulsion means adapted to provide relative movement between said plurality of jointed segments;
  at least one sensor adapted to monitor the angular position of at least one of said plurality of jointed segments;
  a control unit adapted to supervise said propulsion means and to receive feedback information from said at least one sensor so as to facilitate said brace to perform walking patterns;
  whereby the disabled user that wears said gait-locomotor apparatus is able to steadily stand in a stance position supported by said brace, and is able to walk in various walking patterns using said control unit.

Furthermore in accordance with another preferred embodiment of the present invention, said brace comprises a torso brace and a pelvis brace adapted to fit the user's trunk, two thigh braces adapted to fit the user's thighs, and two leg braces adapted to fit the user's legs and feet.

Furthermore in accordance with another preferred embodiment of the present invention, stabilizing shoes are provided and are attached to the brace, said stabilizing shoes are adapted to increase the lateral stability.

Furthermore in accordance with another preferred embodiment of the present invention, said stabilizing shoes are adapted to maintain a side lean.

Furthermore in accordance with another preferred embodiment of the present invention, said stabilizing shoes are provided with a rounded bottom.

Furthermore in accordance with another preferred embodiment of the present invention, said brace is provided with two side crutches adapted to provide direct support to the user.

Furthermore in accordance with another preferred embodiment of the present invention, said two side crutches are retractable so as to facilitate height adjustments.

Furthermore in accordance with another preferred embodiment of the present invention, each one of said two side crutches comprises at least two members that are telescopically connected so as to adjust the side crutch length.

Furthermore in accordance with another preferred embodiment of the present invention, each of said two side crutches is provided with a handle that facilitates the user to grasp the crutches.

Furthermore in accordance with another preferred embodiment of the present invention, said two side crutches are provided with a motorizes system that is adapted to actuate the side crutches and wherein said motorized system is electrically connected to said control unit.

Furthermore in accordance with another preferred embodiment of the present invention, said propulsion means are positioned in or proximal to articulations between the jointed segments of said brace.

Furthermore in accordance with another preferred embodiment of the present invention, said propulsion means are linear motors.

Furthermore in accordance with another preferred embodiment of the present invention, two of said linear motor are adjacent to the user's hip.

Furthermore in accordance with another preferred embodiment of the present invention, two of said linear motors are adjacent to the user's knees.

Furthermore in accordance with another preferred embodiment of the present invention, at least one of the linear motors is provided with a stator provided with a forcer, said stator is attached to one of the jointed segments, and wherein said forcer is coupled to a lever that is attached to the adjoining segment.

Furthermore in accordance with another preferred embodiment of the present invention, said lever having a laterally protruding portion, and wherein said forcer is coupled to said portion.

Furthermore in accordance with another preferred embodiment of the present invention, said stator is pivotally connected to the jointed segment.

Furthermore in accordance with another preferred embodiment of the present invention, said propulsion means is a thrust force motor having a linear motor provided with gearing ability, said linear motor is attached to one of the jointed segments, and wherein a forcer of said linear motor is connected to a belt having two ends, said belt circles about a wheel and is further coupled to a lever attached to the adjoining articulated segment.

Furthermore in accordance with another preferred embodiment of the present invention, said lever is provided with two opposite lateral protrusions, and wherein each of the two ends of said belt is connected to one of the lateral protrusions of said lever.

Furthermore in accordance with another preferred embodiment of the present invention, said lever is a cogwheel that is attached in an articulation between the jointed segments.

Furthermore, on accordance with another preferred embodiment of the present invention, said propulsion means comprises a thrust force motor in which a linear motor having gearing ability is attached to a jointed segment between two articulations, and wherein a stator of said linear motor is provided with two adjacent wheels, said stator is provided with a first forcer coupled to a belt, said belt circles about one of the wheels and circles a cogwheel that is attached adjacent to one of the articulations, and wherein said stator is provided with a second forcer coupled to another belt that circles about the other wheel and circles another cogwheel that is attached adjacent to the other articulation.

Furthermore in accordance with another preferred embodiment of the present invention, said propulsion means is an air muscle actuator.

Furthermore in accordance with another preferred embodiment of the present invention, said propulsion means is a rotary motor.

Furthermore in accordance with another preferred embodiment of the present invention, said rotary motor is positioned in an articulation between the jointed segments of said brace.

Furthermore in accordance with another preferred embodiment of the present invention, two interacting cogwheels, one of the cogwheels is connected by a movable belt to another wheel so as to provide relative movement between the jointed segments.

Furthermore in accordance with another preferred embodiment of the present invention, said two interacting cogwheels are concentric.

Furthermore in accordance with another preferred embodiment of the present invention, said at least one sensor is a tilt sensor.

Furthermore in accordance with another preferred embodiment of the present invention, a goniometer is attached to articulations between the jointed segments of said brace in order to measure the articulation angle.

Furthermore in accordance with another preferred embodiment of the present invention, said at least one sensor is an acceleration sensor.

Furthermore in accordance with another preferred embodiment of the present invention, said at least one sensor is an accelerometer.

Furthermore in accordance with another preferred embodiment of the present invention, said feedback information can be angles of articulation between the jointed segments of said brace.

Furthermore in accordance with another preferred embodiment of the present invention, said feedback information can be accelerations of the user's body parts.

Furthermore in accordance with another preferred embodiment of the present invention, said feedback information can be angular velocities.

Furthermore in accordance with another preferred embodiment of the present invention, a processor is incorporated in said control unit, said processor comprises algorithms.

Furthermore in accordance with another preferred embodiment of the present invention, said algorithms comprises commands dictating the angles between the jointed segments and the position of the jointed segments so as to perform modes of operation on said brace.

Furthermore in accordance with another preferred embodiment of the present invention, said modes of operation are from the group of standing mode, gait mode, climbing mode, descending mode, lie-sit transition mode, sit-stance transition mode, stance-gait transition mode, training mode, learning mode.

Furthermore in accordance with another preferred embodiment of the present invention, at least one of said modes of operation is initiated by exceeding a threshold value in the angular position of at least one of the jointed segments.

Furthermore in accordance with another preferred embodiment of the present invention, at least one of said modes of operation is initiated by receiving a signal monitored by said tilt sensor, said signal exceeds a threshold value in the tilt angle of the user's torso.

Furthermore in accordance with another preferred embodiment of the present invention, said control unit is communicating with said propulsion means through power drivers.

Furthermore in accordance with another preferred embodiment of the present invention, said control unit is communicating with a man-machine interface so as to receive commands from the user.

Furthermore in accordance with another preferred embodiment of the present invention, at least one sensor is communicating with said control unit through feedback interfaces.

Furthermore in accordance with another preferred embodiment of the present invention, said gait-locomotor apparatus further comprises a safety unit and a built-in test unit.

Furthermore in accordance with another preferred embodiment of the present invention, said safety unit is communicating with said control unit.

Furthermore in accordance with another preferred embodiment of the present invention, said safety unit is communicating with said at least one sensor.

Furthermore in accordance with another preferred embodiment of the present invention, said gait-locomotor apparatus is further comprises a power unit.

Furthermore in accordance with another preferred embodiment of the present invention, said at least one sensor provides a warning signal.

Furthermore in accordance with another preferred embodiment of the present invention, a warning signal indicates the status of said battery.

Furthermore in accordance with another preferred embodiment of the present invention, a warning signal indicates currents in said propulsion means.

Furthermore in accordance with another preferred embodiment of the present invention, said gait-locomotor apparatus is further comprises at least one temperature sensor.

Furthermore in accordance with another preferred embodiment of the present invention, said warning signal indicates temperature monitored by the temperature sensor in order to facilitate overheat protection.

Furthermore in accordance with another preferred embodiment of the present invention, said temperature is monitored in said propulsion means.

Furthermore in accordance with another preferred embodiment of the present invention, said temperature is monitored in said control unit.

Furthermore in accordance with another preferred embodiment of the present invention, said gait-locomotor apparatus further comprises a functional electrical stimulation (FES), said FES is electrically connected to said control unit.

Furthermore in accordance with another preferred embodiment of the present invention, said gait-locomotor apparatus further comprises electrodes, said electrodes are electrically communicating with a signal generator so that an electrical signal is transferred by the electrodes.

Furthermore in accordance with another preferred embodiment of the present invention, said signal generator is communicating with said control unit.

Furthermore in accordance with another preferred embodiment of the present invention, said algorithms further comprises commands dictating the electrical signal that is transferred by the electrodes.

In accordance with another preferred embodiment of the present invention, said algorithm further comprises command that activate the FES.

It is thus further provided a method for facilitating disabled user to walk using a gait-locomotor apparatus, said method comprises:
   providing a gait-locomotor apparatus, said gait-locomotor apparatus comprises:
      a brace having a plurality of jointed segments, said brace adapted to fit the lower body of the disabled user;
      propulsion means adapted to provide relative movement between said plurality of jointed segments;
      at least one sensor adapted to monitor the angular position of at least one of said plurality of jointed segments;
      a control unit adapted to supervise said propulsion means and to receive feedback information from said at least one sensor so as to facilitate said brace to perform walking patterns;
   wearing said brace on the user's lower body parts;
   tilting the user's upper body in order to initiate a response in said control unit so as to actuate said propulsion means and to move said brace in order to perform walking patterns;
   commanding said control unit to stop operation or to change actuation;
   whereby the upper body tilts activate and synchronize the gait.

In accordance with another preferred embodiment of the present invention, said method further comprises
   providing electrodes;
   providing signal generator, said signal generator is electrically communicating with said electrodes;
   attaching said electrodes to the user; commanding said control unit to actuate said signal generator.

BRIEF DESCRIPTION OF THE FIGURES

FIG. 9a illustrates a schematic representation of a linear motor with a dual-lever arrangement in accordance with another preferred embodiment of the present invention.

FIG. 9b illustrates a schematic representation of a linear motor with a cogwheel arrangement in accordance with yet another preferred embodiment of the present invention.

FIG. 9c illustrates a schematic representation of a linear motor having double actuation in accordance with an additional preferred embodiment of the present invention.

FIG. 10 illustrates a schematic side view of trunk-to-thigh and thigh-to-leg air-muscle actuators in accordance with an additional preferred embodiment of the present invention.

FIGS. 11a and b illustrate schematic side views of two optional configurations of a geared trunk-to-thigh rotary motors in accordance with yet another preferred embodiments of the present invention.

FIG. 16a illustrates a schematic back view of a left shoe in accordance with a preferred embodiment of the present invention.

FIG. 16b illustrates a schematic side view of the left shoe shown in FIG. 16a.

FIG. 17 illustrates a descent mode algorithm in accordance with a preferred embodiment of the present invention.

DETAILED DESCRIPTION OF THE INVENTION AND FIGURES

The gait-locomotor apparatus of the present invention is a unique motorized brace system for the lower body and lower limbs that is attached to the user's body, preferably under the clothes, and enables the user to restore daily activities, especially stance and gait abilities. In addition to stance and locomotion, the gait-locomotor apparatus supports other mobility functions such as upright position to sitting position transitions and stairs climbing and descending. The gait-locomotor apparatus suits disabilities such as paraplegia, quadriplegia, hemiplegia, polio-resultant paralysis and individuals with severe walking difficulty.

The main purpose of the present invention is to provide a device that allows vertical stance and locomotion by means of an independent device that generally comprises a detachable light supporting structure as well as a propulsion and control means. The gait-locomotor apparatus of the present invention makes it possible to relieve the incompetence of postural tonus as well as reconstituting the physiological mechanism of the podal support and walking. Consequently, the device will reduce the need for wheelchairs among the disabled community; it will provide a better independence and ability to overcome obstacles such as stairs.

Figure 1A:
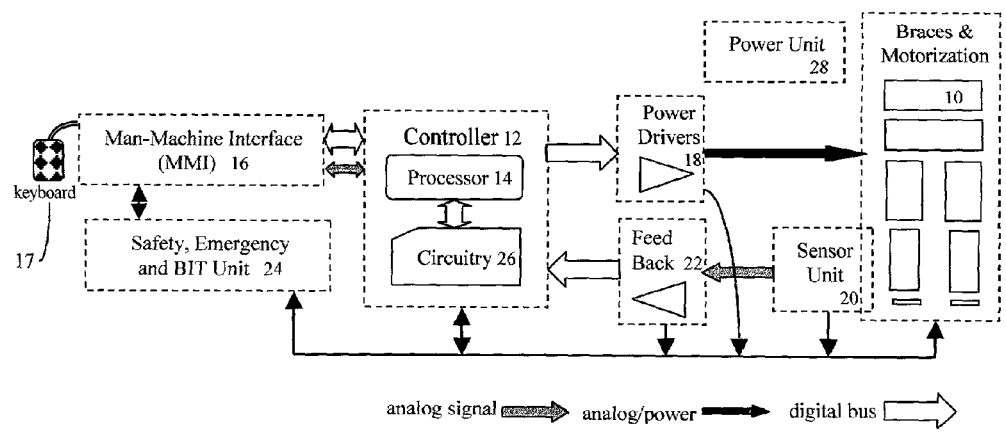
FIG. 1a illustrates a block diagram of a gait-locomotor apparatus in accordance with a preferred embodiment of the present invention.

Reference is now made to FIG. 1a illustrating a block diagram of a gait-locomotor apparatus in accordance with a preferred embodiment of the present invention. The gait-locomotor apparatus of the present invention comprises a brace system 10 that supports parts of the body, such as pelvic corset, thighs and legs orthoses. All the bracing components of brace system 10 are rigid enough so as to support an average body weight, however light enough so it does not impose additional stress on the user's body. Brace system 10 contains means of propulsion (e.g., motors and batteries) that are attached to parts of the lower half of the body and to the limbs as will be comprehensively explained herein after.

A relatively small control unit 12, preferably mounted on the body as well, supervises the motion of brace system 10 and creates stance and gait movements. Control unit 12 executes programs and algorithms in an incorporated processor 14 that constantly interact with movements of the upper part of the body, thus walking patterns and stability are achieved with the help of the user. Control unit 12 commands brace system 10 via power drivers 18. Control unit 12 contains a dedicated electronic circuitry 26, as well. A sensor unit 20 that contains various sensors, monitors parameters of brace system 10 such as torso tilt angle, articulation angles, motor load and warnings, and transfers the information to control unit 12 via feedback interfaces 22. Selective information from the sensors may be transferred also to a safety unit 24. Sensor unit 20 contains components among which are tilt and acceleration sensors that are located on the torso. These sensors sense and measure tilt angles, angular velocities and accelerations.

The gait-locomotor apparatus further comprises a Man-Machine Interface, MMI 16, through which the person controls modes of operation and parameters of the device, such as gait mode, sitting mode and standing mode. Preferably, the user may receive various indications through MMI 16 or to transfer his command and shift motor's gear according to his will through keyboard 17.

The gait-locomotor apparatus further comprises a power unit 28 that preferably includes rechargeable batteries and related circuitry.

Safety unit 24 acts also as an emergency and BIT unit (Built-In Test='BIT') that may accept feedback signals from all components of the gait-locomotor apparatus, and invokes test signals. The purpose of safety unit 24 is to prevent hazardous situations and system failure.

As mentioned, brace system 10 comprises braces and propulsion means. The braces act as a supporting structure that is light and detachable, making it possible to relieve the incompetence of postural tonus as well as reconstitute the physiological mechanism of the podal support and the walking action. The support supplied by the braces is attained from the feet and ankle up, preferably, to the torso depending on the level of injury (in a spinal-cord injury case) or the severity of the disability. Detachable light braces are available commercially. For example, a rigid corset that supports the abdomen and pelvic, and orthoses that support the hip, knee and ankle are manufactured by AliMed Inc. or by Nor Cal Design. Other bracing devices were mentioned herein before in the patent literature (U.S. Pat. No. 5,961,476 and U.S. Pat. No. 4,946,156). The available bracing systems support the torso, thighs, legs and feet and are provided with joints at the locations of the hips, knees and ankles articulations. The brace system of the present invention is generally divided into segments that are adjacent to the trunk, thighs, legs and feet.

Figure 1B:
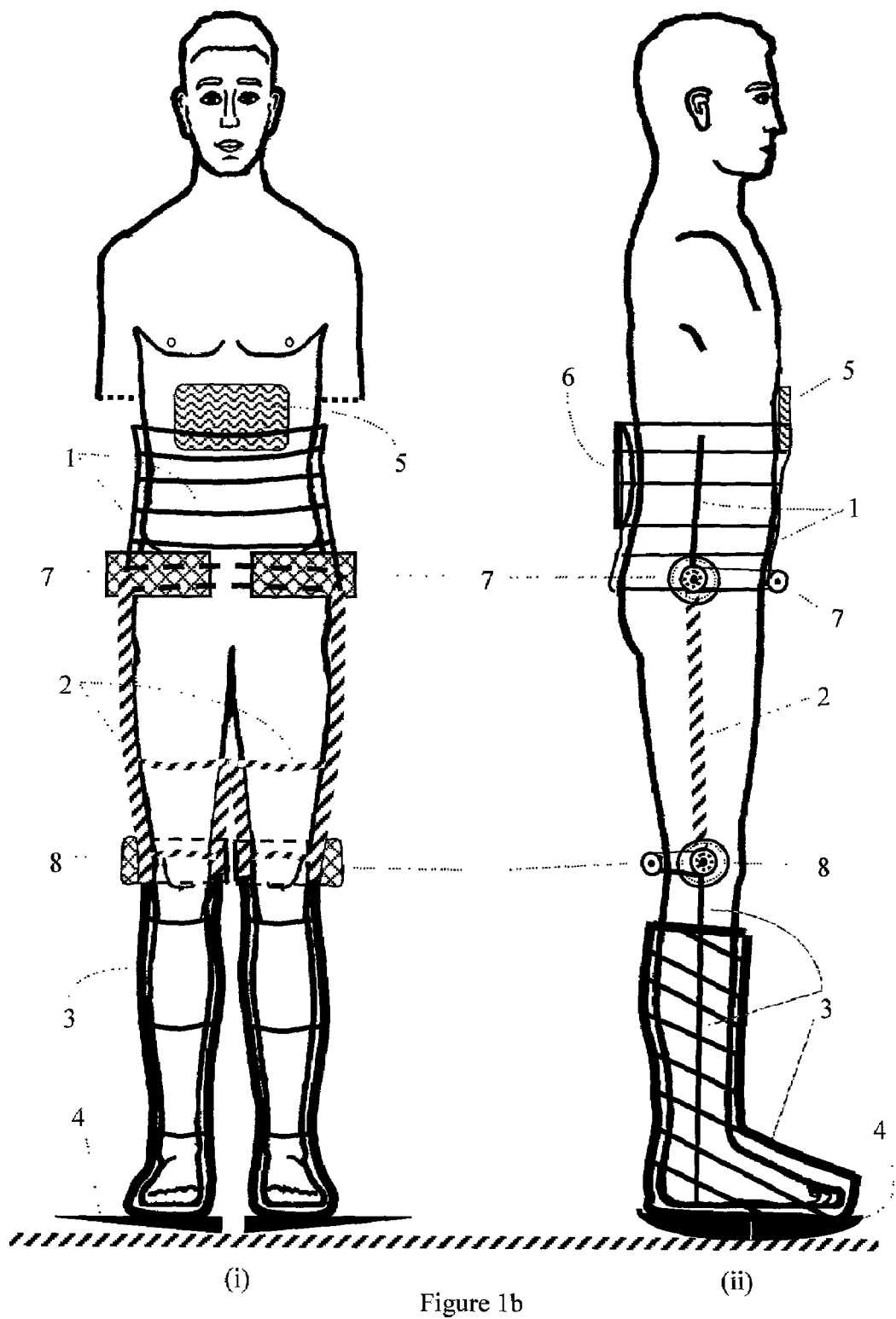
FIG. 1b illustrates a front view (i) and a side view (ii) of a gait-locomotor apparatus in accordance with a preferred embodiment of the present invention, wore by a user.

Reference is now made to FIG. 1b illustrating a front view (i) and a side view (ii) of a gait-locomotor apparatus in accordance with a preferred embodiment of the present invention, wore on a user. As mentioned, the brace segments of the brace system are wore adjacent to the parts of a user's body. A pelvis brace 1 is wore on the trunk, the lower body part. Thigh braces 2 are wore adjacent to the thighs, and leg and feet braces 3 are wore accordingly on the legs and foot. Stabilizing shoes 4 are attached to the bottom of leg and feet braces 3 as will be explained herein after. In the junctions between the segments of the brace system, adjacent to the hip and the knee, hip motors 7 and knee motors 8, respectively, are provided. The motors enable the hip and knee articulations to pivot so as to achieve natural walking movements. Rotary motors such as the ones shown in FIG. 1b (ii) may be applied in the articulations as well as linear motors or any other combination as will be explained comprehensively herein after. The electronic subsystems that comprises the control unit, the sensors, the MMI, the safety unit and the interfaces units are preferably incorporated into an electronic unit 5 that is preferably positioned in the front of the body, below the chest area. A power unit 6 is preferably positioned in the back area. It is optional to separate the electronic units in any other combination and to attach them to any other suitable body part such as pelvis and thigh sides.

The bracing structure may include a mechanism that maintains a desired distance between the legs, thus undesired straddle or joining of the legs is prevented. This spacing mechanism, preferably a combination of flexible metal strips and springs, can be located, as an arc, between the inner sides of the thighs, adjacent the crotch. The spacing mechanism can also be a structure pressing the thighs at their outer sides. In the latter case, the mechanism may include a sort of an oval ring located at the pelvic perimeter, with two extending semi-flexible metal strips at the sides, pressing the thigh braces. The leg-spacing mechanism, can be active (i.e., motorized) or passive (e.g., a flexible metal strip). A passive arrangement, in which the spacing is fixed to an average value, suffices for all practical locomotion purposes, similar to locomotion of normal able-bodied persons.

The braces are provided with a propulsion means that affords a relative movement between various brace system parts. The propulsion means may be any type of motor such as linear motors, air-muscle motors or rotary motors.

Figure 2A:
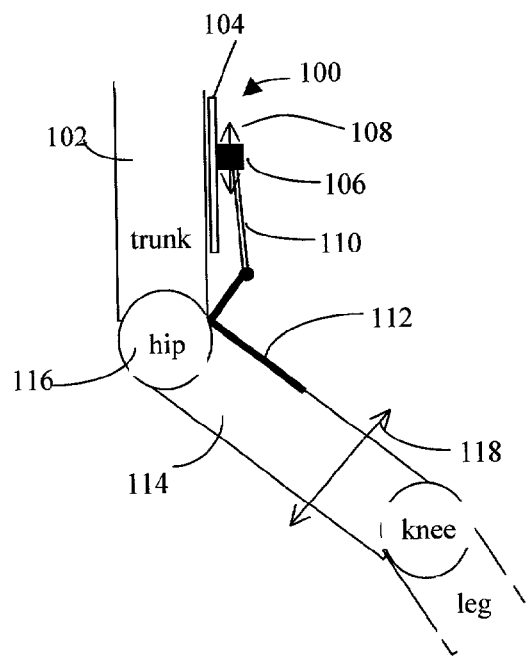
FIG. 2a illustrates a schematic side view of a trunk-to-thigh linear motor in accordance with a preferred embodiment of the present invention.

Reference is now made to FIG. 2a illustrating a schematic side view of a trunk-to-thigh linear motor in accordance with a preferred embodiment of the present invention. A linear motor 100 is adjacent to a trunk 102 of a user. Linear motor 100 comprises a stator 104 that is connected to the brace in a position so that when the user wears the brace, stator 104 is positioned in the frontal portion of the abdomen. A forcer 106 (the rotor of the motor) is the movable part of the motor that moves in the directions that are indicated by arrows 108 upwardly and downwardly on stator 104, and is connected by a connecting means, preferably at least one strip 110, to a lever 112. Strip 110 is adapted to transfer the force of the motor to the lever. A portion of lever 112 is connected or integrated in the brace that is adjacent to the thigh 114 of the user and the other portion that is connected to strip 110 laterally protrudes from the longitudinal direction of the thigh. The protruded portion may be substantially perpendicular to the thigh adjacent portion but may be in any other angle regarding the thigh, as will be explained herein after. When strip 110 is pulled or pushed by forcer 106, thigh 114 may rotate about the hip 116 in the directions indicated by arrows 118. When forcer 106 is in an upward position, thigh 114 is advancing towards trunk 102 performing a pace movement while when forcer 106 is in a downwards position, thigh 114 straightens regarding trunk 102.

Figure 2B:
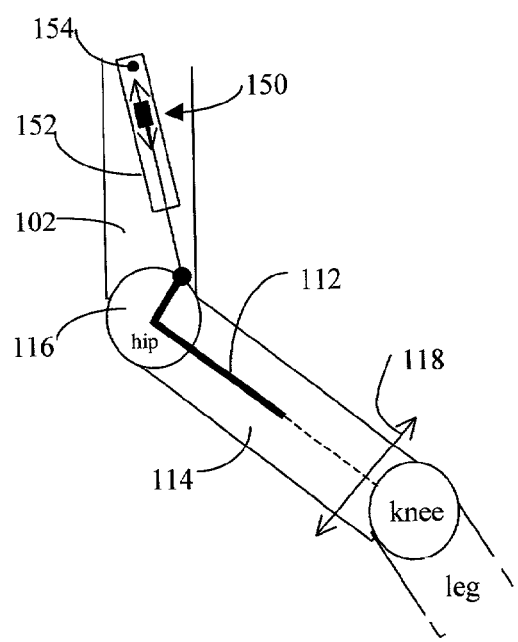
FIG. 2b illustrates a schematic side view of a trunk-to-thigh linear motor in accordance with another preferred embodiment of the present invention.

Reference is now made to FIG. 2b, illustrating a schematic side view of a trunk-to-thigh linear motor in accordance with another preferred embodiment of the present invention. Linear motor 150 is adjacent to the side of trunk 102. Stator 152 is pivotally connected to the brace system that envelops trunk 102 (the brace system is not shown in FIG. 2b) by a pivot pin 154. This arrangement allows linear motor 150 to pivot during the pace and increases the efficiency of the device. Linear motor 150 is connected to a lever 112 having a portion that is adjacent to the thigh and facilitates its upward and downward movements such as in the previously described embodiment.

Figure 3A:
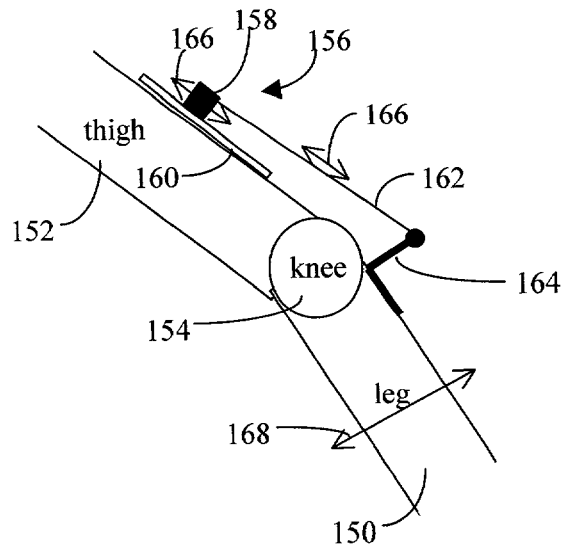
FIG. 3a illustrates a schematic side view of a thigh-to-leg linear motor in accordance with a preferred embodiment of the present invention.

Reference is now made to FIG. 3a illustrating a schematic side view of a thigh-to-leg linear motor in accordance with a preferred embodiment of the present invention. Similar concept as the one used for the pivoting movement of the thigh with regard to the trunk may be applied for the pivoting movement of a leg 150 in regard with the thigh 152 about knee 154. Linear motor 156 is positioned on the brace so that it will be adjacent to thigh 152. Forcer 158 that slides on stator 160, is attached by a strip 162 to a portion of a lever 164 that laterally protrudes from the longitudinal axis of leg 150 or the part of the brace system that is attached to it. The other portion of lever 164 is parallel and adjacent to leg 150. When forcer 158 moves in an upward and downward directions as indicated by arrows 166, the leg pivots in the directions indicated by arrows 168.

Figure 3B:
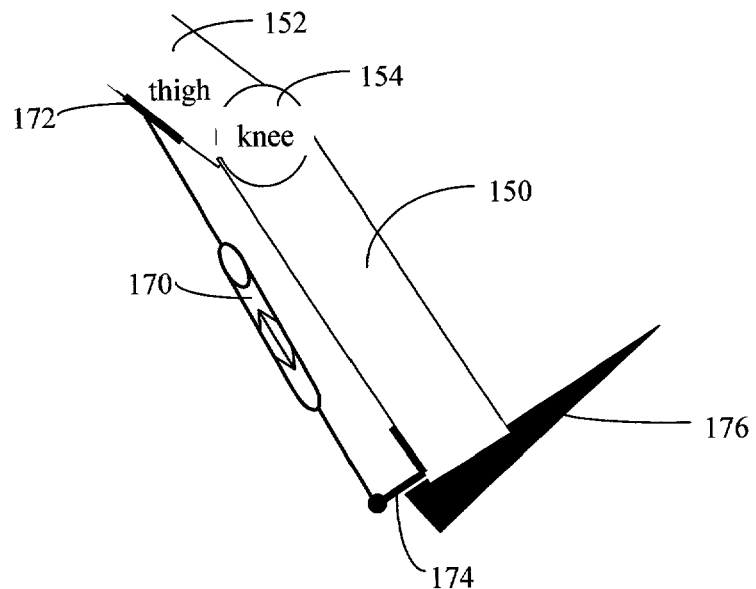
FIG. 3b illustrates a schematic side view of a thigh-to-leg air-muscle motor in accordance with another preferred embodiment of the present invention.

Reference is now made to FIG. 3b illustrating a schematic side view of a thigh-to-leg air-muscle motor in accordance with another preferred embodiment of the present invention. Elongation and contraction activate an air-muscle 170 that is attached at one end to a part of the thigh brace 172 and at the other end, to a lever 174 that is a part of the leg brace. Part of the thigh brace 172 is positioned relatively close to knee 154 in the folding area and lever 174 is positioned on the back of the foot and may be attached to a foot brace 176. When air-muscle 170 is fully elongated, leg 150 is substantially parallel to thigh 152, while when air muscle 170 is contracted, leg 150 is pulled towards thigh 152.

Figure 4:
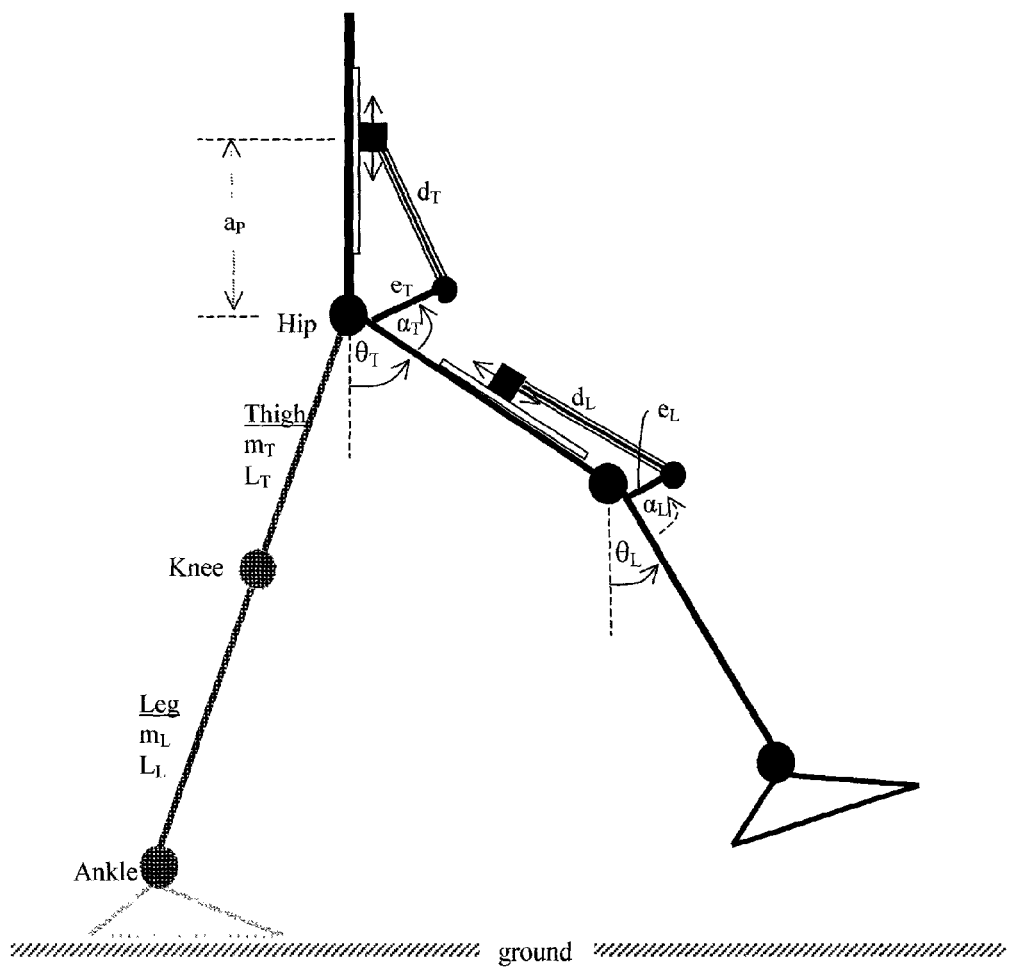
FIG. 4 illustrates a brace-motorization model in accordance with a preferred embodiment of the present invention.

In order to estimate the trust force and the energies required from linear motors such as the ones shown in FIGS. 2a, 2b, 3a and 3b, a human and brace motorization model was built. Reference is now made to FIG. 4 illustrating a brace-motorization model in accordance with a preferred embodiment of the present invention. The model assumes two linear motors (per limb) that are attached to the pelvis/abdomen and to the thigh and actuate a pivotal movement of the hip and the knee, respectively. As explained herein before, the levers are made of two portions, one of which is substantially perpendicular to the thigh or the leg, but may be with any other angle in regard to the other portion, the angle is designated as $\alpha_T$ or $\alpha_L$, as will be explained in the model, and is connected by a strip to the motor. The perpendicular portions that are designated as $e_L$ and $e_T$ are needed to create a leverage. The parameters that are taken into account in the design of the perpendicular portions are:

Power transmission efficiency

Trade-off between thrust force and forcer travel-distance range

The design parameters of the perpendicular portions are their length ($e_L$ and $e_T$) and their tilt angle with respect to the thigh or leg ($\alpha_L$ and $\alpha_T$).

The following parameters are also taken into account:

| | |
|---|---|
| $m_T$: thigh mass | $m_L$: leg mass |
| $L_T$: thigh length | $L_L$: leg length |
| $d_T$: length of the thigh-driving rod | $d_L$: length of the leg-driving rod |
| $\theta_T$: angle between thigh and ground normal in the gait mode, or, between torso prolongation and thigh in other modes. | $\theta_L$: angle between leg and ground normal in the gait mode, or, between torso prolongation and leg in other modes. Note that: $\theta_{LMIN} \leq \theta_L \leq \theta_T$ |
| $e_T$: length of the thigh-brace extension | $e_L$: length of the leg-brace extension |
| $\alpha_T$: thigh-brace extension tilt angle with respect to the thigh | $\alpha_L$: leg-brace extension tilt angle with respect to the leg |
| $a_P$: distance between thigh forcer and the hip | $a_T$: distance between leg forcer and the knee |
| $a_{Pmin}$: the minimum value of $a_P$ | $a_{Tmin}$: the minimum value of $a_T$ |
| $R_T$: range (travel distance) of the thigh forcer | $R_L$: range (travel distance) of the leg forcer |
| Fmotor$_T$: thrust force of the thigh motor | Fmotor$_L$: thrust force of the leg motor |

Figure 5A:
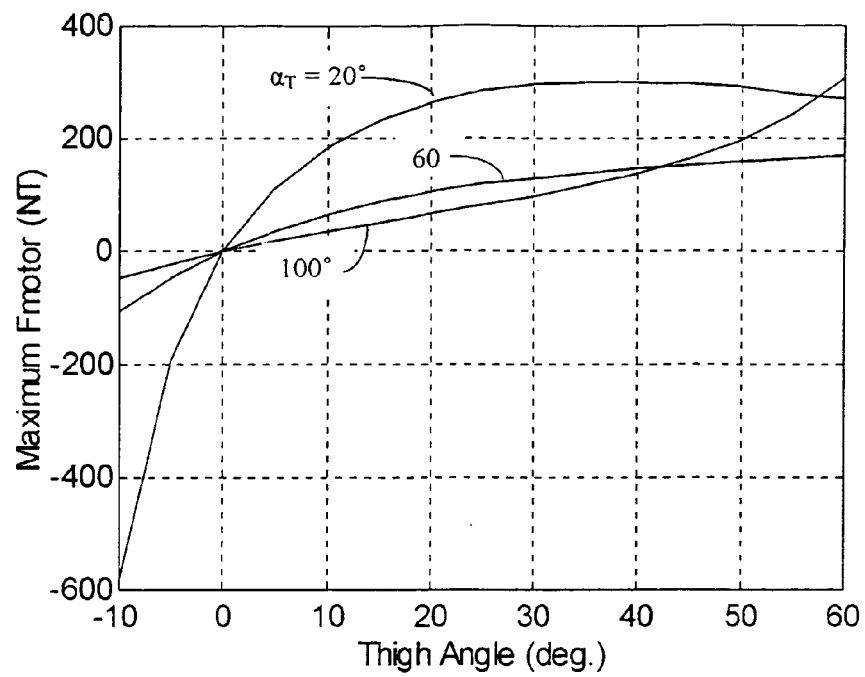
FIG. 5a illustrates graphically the maximum required thigh-motor force versus thigh angle ($\theta_L = \theta_T$) for various tilt angles, $\alpha_T$. The calculations were conducted with respect to the model shown in FIG. 4.
Figure 5B:
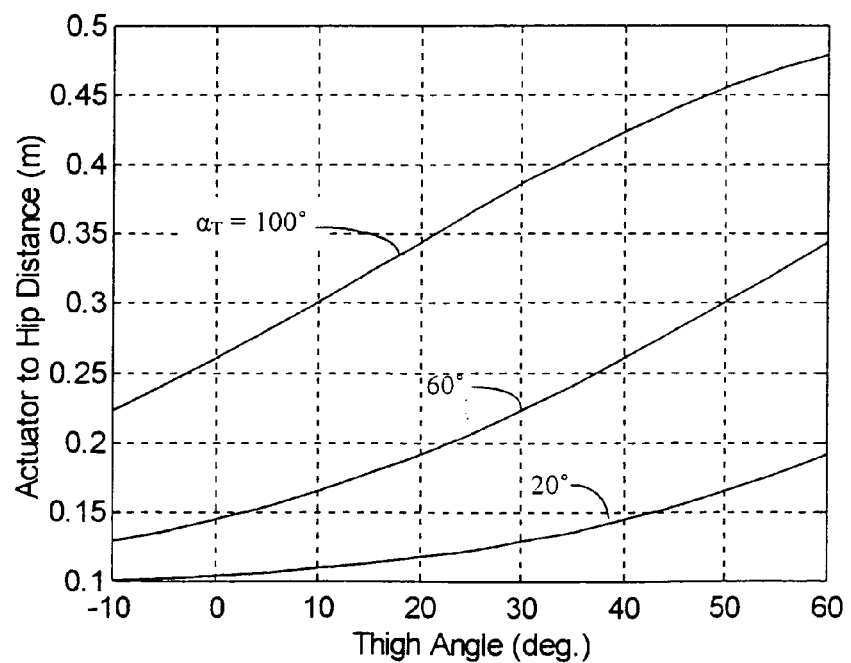
FIG. 5b illustrates graphically possible forcer-to-hip distance versus thigh angle ($\theta_T$) for various tilt angles $\alpha_T$. The calculations were conducted with respect to the model shown in FIG. 4.
Figure 6:
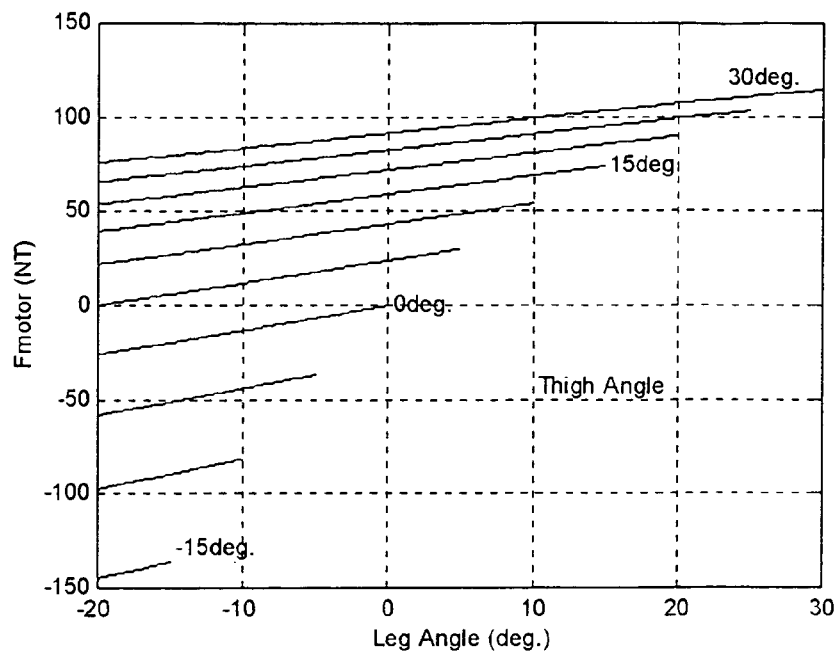
FIG. 6 illustrates graphically possible thigh-motor thrust force versus leg angle ($\theta_L$) for various thigh angles, $\theta_T$. The leg angle for each thigh angle ranges from −20° to $\theta_L = \theta_T$ (straight limb). $\alpha_T = 70°$. The calculations were conducted with respect to the model shown in FIG. 4.

Reference is now made to FIGS. 5–8 that illustrate the thrusting forces needed to support a walk. FIGS. 5 and 6 correspond to the thigh motor and FIGS. 7 and 8, to the leg motor. The calculations were carried out using the following exemplified values for the former parameters:

| | |
|---|---|
| $m_T$ = 8 Kg | $m_L$ = 4 Kg |
| $L_T$ = 40 cm | $L_L$ = 40 cm |
| $-10° \leq \theta_T \leq 60°$ | $-10° \leq \theta_L \leq \theta_T$ |
| $e_T$ = 20 cm | $e_L$ = 10 cm |
| $a_{Pmin}$ = 10 cm | $a_{Tmin}$ = 20 cm |
| $\alpha_T$ = 70° | $\alpha_L$ = 110° |

FIGS. 5 and 6 address the thigh motor. FIG. 5a depicts the maximum required force ($F_{motor}$ in NT) versus the thigh angle ($\theta_T$) Maximum $F_{motor}$ or maximum torque is obtained by setting $\theta_L = \theta_T$. FIG. 5b depicts the forcer-to-hip distance, $a_p$, or the forcer travel distance, $R_T$, versus the thigh angle ($\theta_T$). The plots illustrate various tilt angles ($\alpha_T$) of the perpendicular portion in regard to the thigh.

In this example, choosing $\alpha_T$ between 40° and 55° yields good combinations of low travel distance and force. The required thrust force is about 200 NT and the forcer travel range for $-10° \leq \theta_T \leq 60°$ is about 16 cm. Smaller range can be traded for larger thrust. Normal gait doesn't require thigh angles larger than 25°, and in that case the peak thrust is less than 150 NT and forcer range of about 6 cm (for $\alpha_T = 55°$).

FIG. 6 exemplifies thrust force versus leg angle, $\theta_L$, for various thigh angles, $\theta_T$. The leg angle, for each thigh angle, ranges here from $-20°$ to $\theta_L = \theta_T$ (strait limb), the laterally protruded portion's tilt angle is $\alpha_T = 70°$.

Figure 7A:
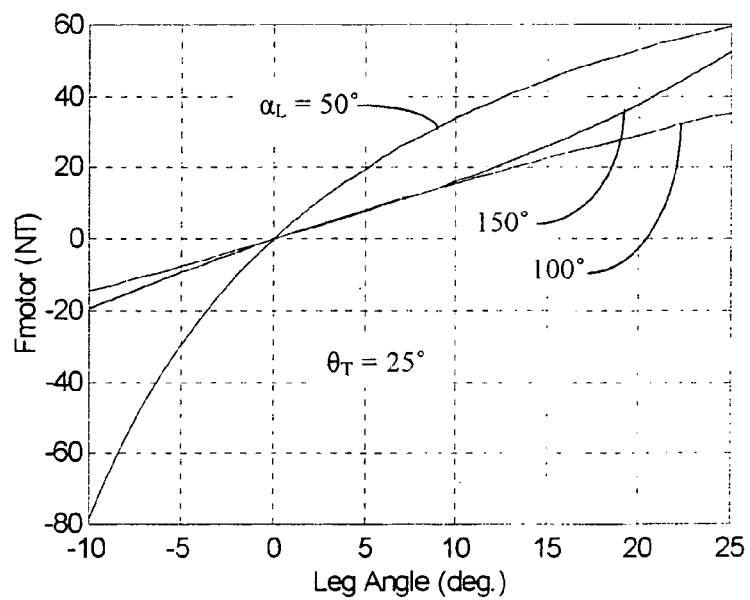
FIG. 7a illustrates graphically possible required leg-motor force versus leg angle ($\theta_T = 25°$) for various tilt angles, $\alpha_L$. The calculations were conducted with respect to the model shown in FIG. 4.
Figure 7B:
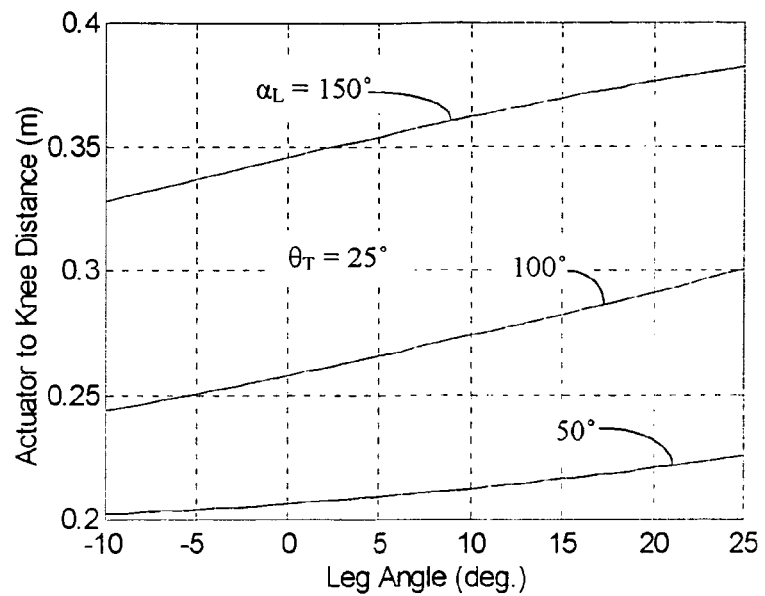
FIG. 7b illustrates graphically possible forcer-to-knee distance versus leg angle ($\theta_T = 25°$) for various tilt angles $\alpha_L$. The calculations were conducted with respect to the model shown in FIG. 4.
Figure 8:
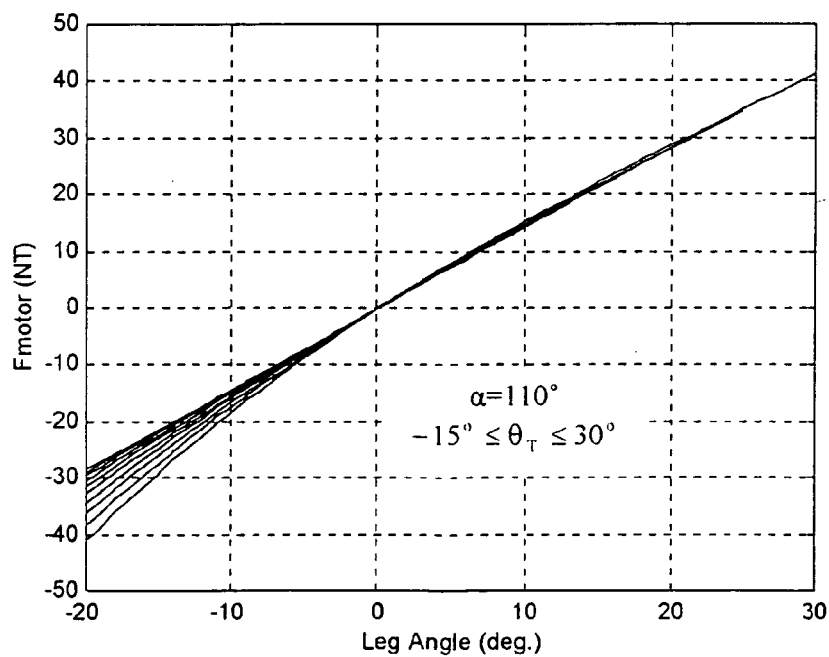
FIG. 8 illustrates graphically possible leg-motor thrust force versus leg angle ($\theta_L$) for various thigh angles, $\theta_T$. The leg angle for each thigh angle ranges from −20° to $\theta_L = \theta_T$ (straight limb). The calculations were conducted with respect to the model shown in FIG. 4.

FIGS. 7 and 8 address the leg motor. FIG. 7a depicts the required force ($F_{motor}$ in NT) versus the leg angle ($\theta_L$) for thigh angle $\theta_T = 25°$. FIG. 7b depicts the forcer-to-knee distance, $a_T$, versus the leg angle. The plots illustrate various tilt angles ($\alpha_T$).

The conclusions that may be withdrawn from the above exemplified data are that a thrust force of 40 NT is sufficient for a travel range of 6 cm in the above example. Smaller range will require higher thrust. Note that $\alpha_L = 110°$ yields the good combination of low travel distance and force. Other motor locations and extension dimensions will result in different optimum α values.

FIG. 8 exemplifies thrust force versus leg angle, $\theta_L$, for various thigh angles, $\theta_T$. The leg angle, for each thigh angle, ranges from $-20°$ to $\theta_L = \theta_T$ (strait limb). The energy required to support a walk is calculated as an example and the energy required from the motorized brace system of the present invention and consequently the energy efficiency and the expected walking range for the above example are presented. The desired energy required to lift the leg from 0° to $\theta_L$, is given by:

$$E_L = m_L g L_L \sin^2 \frac{1}{2} \theta_L,$$

in the model. For example, for $\theta_L = 30°$ the energy required is $E_L = 1.05^{joules}/_{step}$.

Similarly, the desired energy required to lift the thigh from 0° to $\theta_T$, is given by:

$$E_T = (m_T + 2m_L) g L_T \sin^2 \frac{1}{2} \theta_T,$$

which yields, for $\theta_T = 30°$, $E_T = 4.20^{joules}/_{step}$. It was assumed that a single step is initiated by a backward lifting of thigh and leg ($\theta_T$ and $\theta_L$ are negative) and continued by forward lifting of the thigh and straitening or almost straitening the leg ($\theta_L \rightarrow \theta_T$). Furthermore, the kinetic energy is neglected due to low velocities. Designate the initial thigh and leg angles as $\theta_{T\ INIT}$ and $\theta_{L\ INIT}$ respectively, the total energy required to support a stride is given by:

$$E_s = m_L g L_L \left( \sin^2 \frac{1}{2} \theta_{L\cdot INIT} + \sin^2 \frac{1}{2} \theta_L \right) +$$
$$(m_T + 2m_L) g L_T \left( \sin^2 \frac{1}{2} \theta_{T\cdot INIT} + \sin^2 \frac{1}{2} \theta_T \right)$$

In the above example given herein, substituting $|\theta_{T\ INIT}|=|\theta_T|$ and $|\theta_{L\ INIT}|=|\theta_L|$ yields $E_s=10.5^{joules}/_{step}$.

Therefore, the preferred parameters for this example required are:
Velocity: 1 m/s (3.6 km/h)
Step size: 40 cm Under these requirements, the energy and power consumption are $26.2^{joules}/_m$ (10.5 joules×2.5 steps) and 26.2 W respectively. Thus, for example, a battery of 12V & 10 Ah (432 kjoule), for the whole system, supports a walking range of 16 km, without taking into account efficiencies.

Parameters of available linear motors were used in order to calculate the required energy. The assumptions were as follows:
Thigh and leg angles, $\theta_T$ and $\theta_L$, are bounded in a normal walk to ±30° and the average angle is assumed to be 15°.
From inspecting FIGS. 6 and 8, thrust forces of 140 NT for the thigh and 30 NT for the leg were chosen.
The motor driver ('H' bridge) has a 95% efficiency.

Under the above assumptions and examples, a thigh motor requires about 75 W and the leg motor requires about 35 W. For a step (0.4 sec), the energy requirement that was obtained is $46^{joules}/_{step}$. Thus, the overall efficiency is 23%, and the walking range is 3.6 km (for a 12V & 10 Ah battery).

The above model and calculations support a normal gait. Supporting climbing and sit-to-stance transient, where the load is about five times heavier, requires larger linear motors or other practical solutions. One solution is to use an external support, such as a walking frame or railing. Another possible solution is combining gears with the linear-motor system in order to produce larger torque on the expense of velocity.

Reference is now made to FIGS. 9a, 9b and 9c illustrating other schematic representations of linear motors in accordance with other preferred embodiments of the present invention. FIG. 9a depicts dual-lever arrangement and FIG. 9b depicts cogwheel arrangement. The advantage of these embodiments is in the ability to introduce a gearing system in order to increase the thrust force. As was already explained, the thrust computed in the model explained herein above suffices to support a normal walk; however, supporting sitting-to-standing transitions or stairs climbing (without an external use of walking frame), requires greater force that may be incorporated by using a gear.

The configuration shown in FIG. 2b, requires asymmetric forces for positive and negative thigh angles, see FIG. 5b (a larger force is required for negative angles). The configurations presented in FIG. 9 adjust that situation and as a result, lower thrust force is required. In FIG. 9(a), linear motor 200 is preferably positioned on the side of a trunk 202 so that they will not interfere with the sitting position. A forcer 204 of linear motor 200 is attached to a belt 206 that circles about a wheel. Both ends of belt 206 are connected to a lever 210. Lever 210 has a dual arrangement; it has two extensions 212 on both sides of lever 210 that are adjacent to thigh 214 and together they form a T shaped lever. When forcer 204 moves, it pulls the belt that in turn pushes or pulls extensions 212, causes thigh 214 to pivot in respect to hip 216.

The implementation shown in FIG. 9b uses a combination of a cogwheel 250 as a gear in order to increase torque. Belt 206 that circles wheel 208, circles also cogwheel 250 that is a part of a thigh brace (not shown in the Figure) so that it is positioned in the side of hip 216.

The motorized system shown in FIG. 9c depicts a linear motor 220 having a stator 222 on which a first forcer 224, which is the thigh forcer, and a second forcer 226, which is the leg forcer, are driven. Two adjacent double-deck wheels 228 are attached on stator 222 between both forcers; both wheels are not correlated. Similarly to the cogwheel arrangement shown in FIG. 9b, first forcer 224 is attached to a belt 230 that circles one of double-deck wheels 228 on one side and a cogwheel 232 on the other side. Cogwheel 232 is a part of the trunk brace (not shown in the figure) and is adjacent to hip 216 so that the movement of first forcer 224 causes the hip to pivot. Oppositely, second forcer 226 is attached to a belt 234 that circles one of double-deck wheels 228 on one side and a cogwheel 236 on the other side. Cogwheel 236 is a part of the leg brace (not shown in the figure) and is adjacent to knee 238 so that the movement of second forcer 226 causes leg 240 to pivot about thigh 314. The arrangement illustrated in FIG. 9c is preferable since is has the advantage of motorization compactness that reduces possible cumbersome of the brace system.

Reference is now made to FIG. 10, illustrating a schematic side view of trunk-to-thigh and thigh-to-leg air muscle actuators in accordance with an additional preferred embodiment of the present invention. An air muscle provides a pulling force by contracting. Air muscle is a known actuator that behaves in a similar way to a biological muscle; it is a pneumatic device (tube) that contracts by thickening when pumped up with air. A leverage system having a first portion 300 adjacent to a trunk 302, a second portion 304 adjacent to a thigh 306 and a third portion 308 adjacent to a leg 310 is attached to the brace (not shown in FIG. 10). On the junctions between the three portions of the leverage system, extensions are provided on both sides of the leverage system; first extensions 312 are connected to second portion 304, which is adjacent to hip 314 and second extensions 316 are extended from third portion 308, in the area of a knee junction 318. Two parallel air muscles 320, each air muscle is counterbalanced by an opposite muscle similarly to the way it is done in the human body, are connected at one end to lever 300 and at the other end to one of extensions 312. Similarly, two air muscles 322 are connected between lever 304 and extensions 316.

Another solution for the increased torque is using rotary motors with gears. Reference is now made to FIG. 11 illustrating schematic side views of two optional configurations of a trunk-to-thigh rotary motor in accordance with yet another preferred embodiment of the present invention. Rotary motors gain the following advantages: a. it is easy to combine gears in the rotary motors; b. there is a large selection of available products. In configuration (a), rotary motor 350 is a motor for hip motorization, however, similar motors may be introduced in the knee articulation as well. In the case of knee motorization, the motor can be placed behind the knees or at the sides. Rotary motor 350 are located in front of hips 352 or at the sides so that they do not disturb a sitting position. Rotary motor 350 is provided with a wheel 354 and a cogwheel 356 that are circled by a movable belt 358. Cogwheel 356 is preferably connected to a pelvic brace (the braces are not shown in FIG. 11). Cogwheel 356 is interacting with another cogwheel 360 that is preferably attached to the thigh brace in order to provide the gearing possibilities. In configuration (b) shown in FIG. 11, both cogwheels are concentric. The advantage of the configuration shown in FIG. 11b is its compactness.

Returning to FIG. 1, sensor unit 20 monitors parameters of brace system 10 and transfers the information to control unit 12 via feedback interfaces 22. The sensor unit may supply the following information:

Hip and knee angles
Various body-part accelerations
Torso tilt angle and angular velocity and the following warning signals:
Battery status
Motors currents (over-current protection)
Components temperatures (motors, power circuitry etc.- overheat protection).

Other warnings can be derived from the data signals.

The hip and knee articulation angles may preferably be measured by a goniometer. Goniometers are known in the art and are basically potentiometers that may be located at the joint and produce voltage that is proportional to the joint angle. An example of a goniometer that may be incorporated in the gait-locomotor apparatus of the present invention is disclosed in Finley, F. R., and Kapovich, P. V., "Electrogoniometric Analysis of Normal and Pathological Gaits", Res. Quart. 35, 379–384 (1964).

Accelerations of various body parts may preferably be measured by an accelerometer. Accelerometers are known in the art and their principle of operation is disclosed, for example, in Morris, J. R. W., "Accelerometery—A Technique for the Measurements of Human Body Movements," J. Biomech. 6, 729–736 (1973). The device is basically a bridge with a mass, where movements of the mass cause deviation from balance.

Torso tilt angle and its derivatives (angular velocity and acceleration) are preferably obtained by tilt sensors. Tilt sensors, for example, are manufactured by E.G. Crossbow Technology Inc. The tilt sensors may be located on the torso. The signals that are obtained through the tilt sensors may be used in order to initiate a step, since an upper-body tilt is interpreted as a fall to be prevented by a corresponding step. It is emphasized that the initiation of the gait-locomotor apparatus is established by intentional tilts of the body; thus fully participating the disabled user in the walking initiation and progress so that the user is a part of the decision making process.

As mentioned herein above, control unit 12 supervises the motion of brace system 10 and communicated with sensor unit 20 directly or through interfaces. The controller supports the following modes of operation:

1. Stance
2. Gait and stance-to-gait transition
3. Lie-sit-stance transitions
4. Climb (e.g., stairs)
5. Descent (e.g., stairs)
6. Trainer
7. Test
8. Learn/Adapt Control unit 12 produces signals to power drivers 18 that motorize brace system 10, and receives feedback from sensor unit 20. The feedback from the sensors is necessary for performing a closed-loop algorithm of modes 1 to 6 as will be explained herein after. In the trainer mode, the gait-locomotor apparatus is in its capacity as an active/passive trainer (e.g., bicycling). Test mode uses the safety unit 24 to insure a proper operation; control unit 12 initiates test signals and monitors the resultant feedback signals.

In the 'Learn/Adapt' mode, the algorithm adapts to the user, i.e., the system 'learns', preferably by applying neural network algorithm, and acquires the various parameters needed for the operational modes.

Control unit 12 is provided with a processor 14 that employs closed-loop control algorithms jointly with user involvement. The closed-loop control algorithms and the user are interacting in order to establish a gait, transition or any other mode of operation. The user is involved mainly in selecting the mode of operation 1–8, and in performing intentional upper-body movements.

Figure 12:
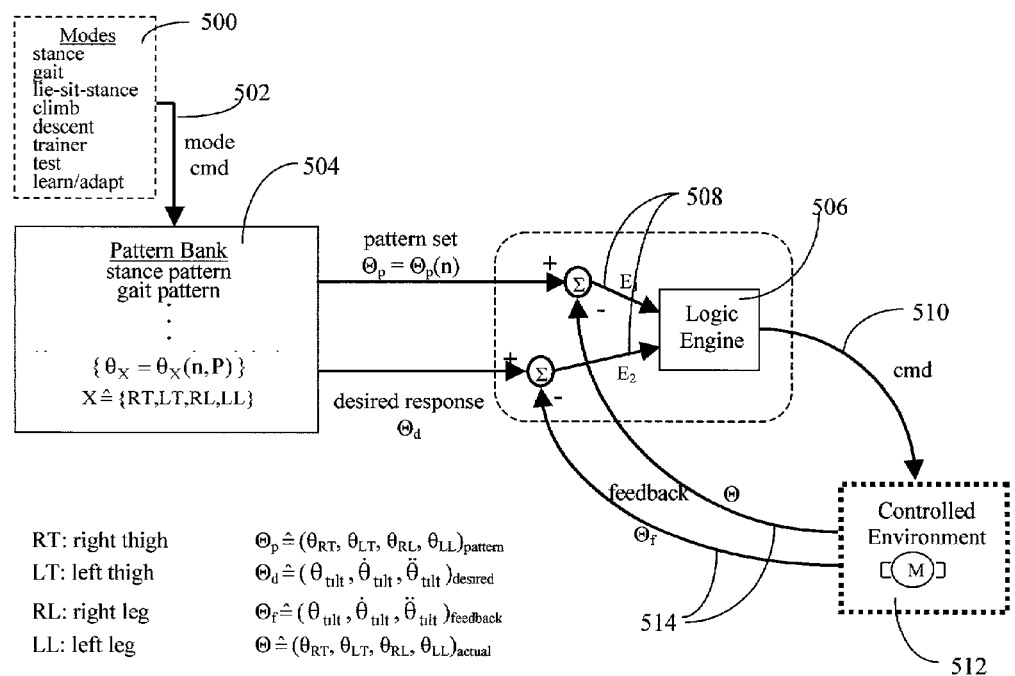
FIG. 12 illustrates a schematic schema for real-time control realization in accordance with a preferred embodiment of the present invention.

Reference is now made to FIG. 12 illustrating a schematic schema of real-time control in accordance with a preferred embodiment of the present invention. Selecting the above-mentioned modes of operation 500 is performed through a mode command 502. Mode command 502 enters a pattern bank 504 that contains sets of time (index) and mode dependent patterns, $\{\Theta=\Theta(n,P)\}$, where 'n' is the time index and 'P' is the modal parameter. Each specific pattern or a time function represents a certain mode or situation in the gait-locomotor apparatus of the present invention. Pattern bank 504 supplies the desired functional dependence of the angles to be controlled, $\Theta=(\theta_{RT}, \theta_{LT}, \theta_{RL}, \theta_{LL})$, on the time index, i.e., $\Theta_p=\Theta_p(n)$. The time scale is determined in a logic engine 506 in a real-time adaptive process that is mainly influenced by the torso tilt angle and its derivatives, angular velocity and acceleration. Logic engine 506 accepts error signals 508: $E_1=\Theta_p-\Theta$ and $E_2=\Theta_d-\Theta_f$ and outputs a motor command 510. In order to minimize the errors' magnitude, numerous algorithms and methods exist, including fuzzy logic.

In order to better understand the operation of the control unit, a gait initiation is discussed herein, for example. In assuming a stance mode in which $\Theta_f=(\theta_{tilt},\dot{\theta}_{tilt},\ddot{\theta}_{tilt})\approx(0,0,0)$, i.e., the tilt vector is zero in the fuzzy sense, and also $\Theta\approx(0,0,0,0)$. The user selects a gait mode using mode command 502, and the proper pattern, $\Theta_p(n)$, is loaded from pattern bank 504 into logic engine 506. Next, the user tilts its upper body forward, beyond some threshold angle, and errors $E_1$ and $E_2$ 508 attain high magnitude values (the desired tilt vector is $\Theta_d\approx(0,0,0)$). The process of minimizing the errors' magnitude results in a formation of a forward step that prevents a fall. The step is only partially defined by the vector $\Theta_p$ logic engine 506 uses the tilt angle and its derivatives (via $E_2$) to generate the following parameters:

Boundaries or magnitudes of the hip and knee angles, $\Theta_{max}=(\theta_{RT}, \theta_{LT}, \theta_{RL}, \theta_{LL})_{max}$.

Rate of the process or time scale (sampling frequency 1/T).

A pace is created when the initial step is followed by a periodically swing of the torso between upright and tilt positions. The time period of the torso swing controls the walk velocity. A gait pattern, $\Theta_p(n)$, of a single limb is exemplified in the table herein after. The gait is divided into six phases that are also illustrated in FIG. 20.

Figure 20:
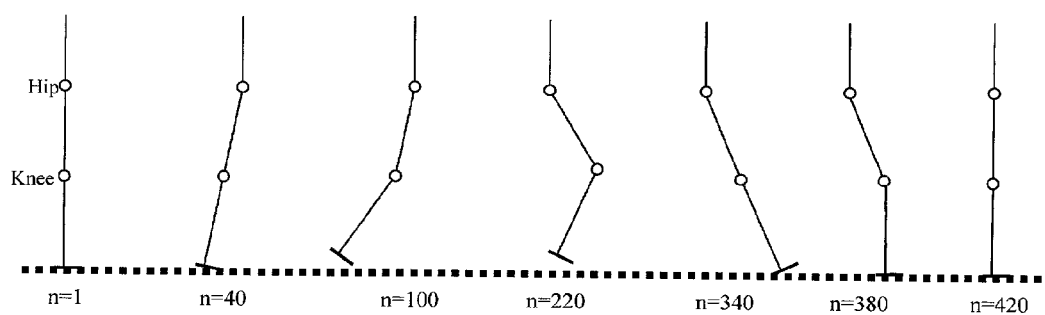
FIG. 20 illustrates exemplified gait pattern phases of a single limb in accordance with a preferred embodiment of the present invention.

Reference is now made to FIG. 20 illustrating gait pattern phases of a single limb in accordance with a preferred embodiment of the present invention. The gait pattern is demonstrated via a cyclic table (n=1 corresponds to n=420: the limb is strait and perpendicular to the ground). Alternately, a pattern can be generated using functions of the sort: $\theta(n)=\theta_0+K(n)\delta\theta$, where K is phase (and feedback) dependent and $\delta\theta$ is the angle increment. The latter method may consume less memory.

by user hand support or, if not possible, by an external support 600. In the final position on the edge of the bed, the legs reach 0° (legs parallel to torso). In the stance position 608, the limbs must be straitened ($\theta_T$: 90°→0°, $\theta_L$: 0°→0°),

| degrees | | Phase 1 | | | Phase 2 | | Phase 3 | Phase 4 | | | Phase 5 | | | Phase 6 | |
|---|---|---|---|---|---|---|---|---|---|---|---|---|---|---|---|
| | $\theta_T$ | 0 | -.25 | ... -10 | -10 | ... -10 | ... 20 | 20 | ... | 20 | 19.8 | ... | 10.0 | ... | 0 |
| | $\theta_L$ | 0 | -.25 | ... -10 | -10.3 | ... -25 | ... -10 | -9.8 | ... | 20 | 19.8 | ... | 0.0 | ... | 0 |
| | $\theta_{T-L}$ | 180 | 180 | ... 180 | 179.8 | ... 165 | ... 150 | 150.3 | ... | 180 | 180 | ... | 170 | ... | 180 |
| | n | 1 | 2 | ... 40 | 41 | ... 100 | ... 220 | 221 | ... | 340 | 341 | ... | 380 | ... | 420 |

Time Index ⟶

The gait pattern of the two limbs is substantially identical, with one pattern cyclically shifted with respect to the other.

Returning to FIG. 12, the system is controlled while providing feedback signals 514.

As indicated here in the above example, the motion commands from control unit 12 are synchronized with the user's intentional body movements. The intentional body movements are basically divided into three categories:

1. Upper-body tilt.
2. Body 'throwing' or applying abrupt angular torque.
3. Use of external supports such as walking frame and railing.

Since walking action may be visualized as a series of prevented falls, upper-body tilt that is detected by sensor unit 20 can be interpreted by control unit 12 as a fall. As a result of an upper-body tilt, a step is initiated by control unit 12 through power drivers 18. Thus the upper-body tilt is incorporated in the gait algorithm.

Figure 13:
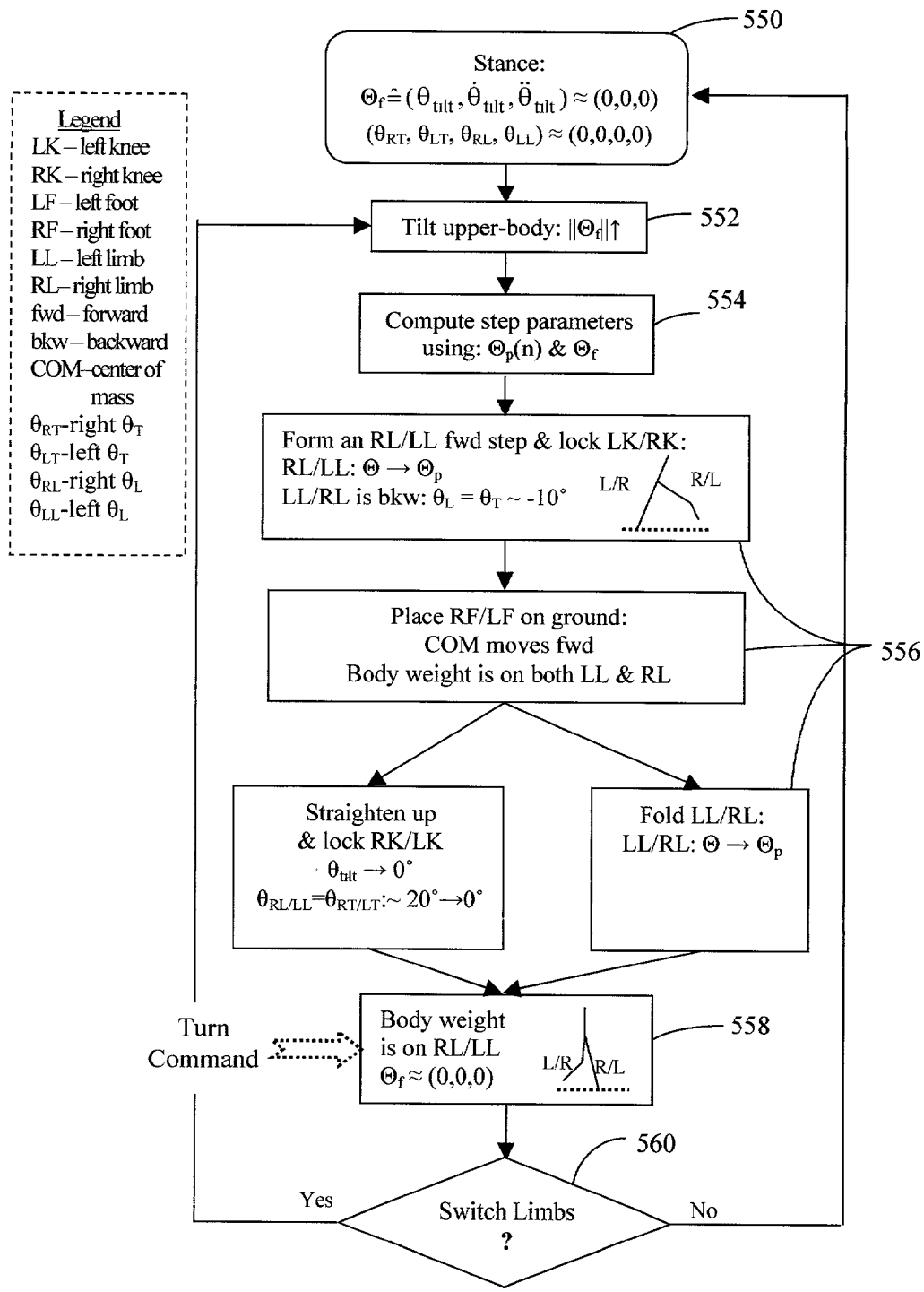
FIG. 13 illustrates a gait mode algorithm in accordance with a preferred embodiment of the present invention.

Reference is now made to FIG. 13 illustrating a gait mode algorithm in accordance with a preferred embodiment of the present invention. As mentioned herein before, the gait mode is initiated from stance mode parameters 550. The user tilts his upper body by voluntary upper body movement 552. The algorithm computes the step parameters 554 using tilt angle and its derivatives and controls the step magnitude (via the magnitudes of the hip and knee angles) and the pace rate using a pattern from the pattern bank shown in FIG. 12. Movements of the limbs 556 are performed using the motors so as to perform a step. Turning while walking is accomplished by the user's body motion, in this case, upper-body 'throwing' that applies abrupt angular torque on the leg that carries the body weight. In a turn command 558 the leg of the user serves as an axis for the turn. After one step is accomplishes with one limb, the other limb goes through a similar procedure, is desired 560.

Figure 14:
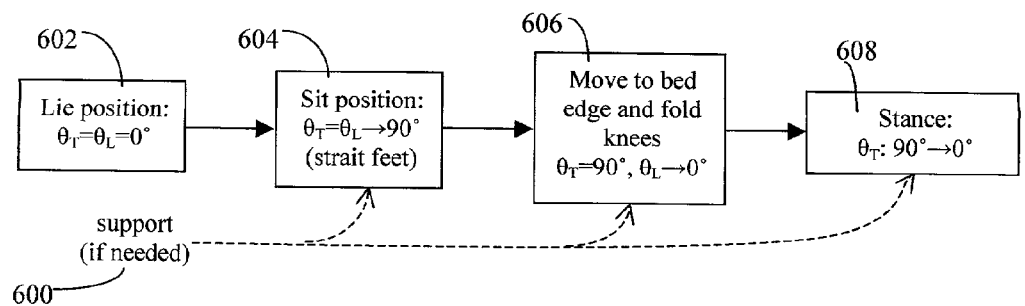
FIG. 14 illustrates a lie-sit-stance transition procedure in accordance with a preferred embodiment of the present invention.

Reference is now made to FIG. 14 illustrating a lie-sit-stance transition procedure in accordance with a preferred embodiment of the present invention. Commanding the motors is partly done manually by the user or by the user aid. The amount of the external support 600 depends on the level of the user disability. The user puts the gait-locomotor apparatus of the present invention, preferably under the cloths, while the limbs are strait and may be locked by the motors, in a lie position 602. The user activates the hip motors until sit position 604 is gained; it is preferable that the motors will be stoped automatically. The knees are still locked. The user activates the leg motors in order to place the legs on the floor. For that purpose, the user is situated on the bed edge 606. Stability is maintained in any of the stages which means that the leg motors have to rotate the knee articulations (up to 90°) in order to maintain $\theta_L=0°$. Two pairs of motors are operated in an alternating fashion (hips-knees-hips . . . etc.) while using small increments to maintain stability in stance position 608.

Automatic control of the sit-to-stance transition, i.e., simultaneous activation of all motors by the controller, may involve pre-acquired parameters. These parameters (namely tilt angle as function of the hip and knee angles during the transition) are measured and stored during the learning phase of the system ('Learn/Adapt' mode). The motor system for the transitions should be in its low gear, while shifting the gear may be done manually.

As mentioned, the major task in the stance mode is maintaining stability. The following mechanisms of control are used in the stance mode: Upper-body movements; Rapid and small forward and backward steps; and external support, such as a walking frame. As for the upper-body movements, the stability is kept similarly to persons that are not disabled. However, since it might not suffice, a second mechanism is automatically activated by the controller, based on feedback (tilt angle, angular velocity and acceleration) from the sensor unit. The algorithm for the second mechanism is similar to gait initiation as discussed herein before. The use of the walking frame depends on the severity of the disability.

Two additional means of stabilization are hereby suggested:

1. Bent knees: During gait and particularly during stance, a slight bent of the knees (unlocked knees: $\theta_L<\theta_T$) will increase the stability, as actually happens in persons with no disabilities. No additional effort, in this case, is requested from the user.
2. Side poles: A significant increase in the stability, particularly in the lateral stability, can be achieved by locating crutches at the body sides.

Figure 15:
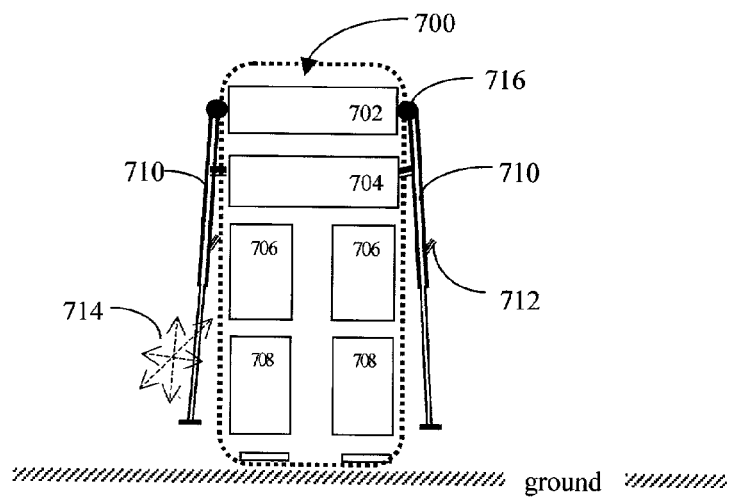
FIG. 15 illustrates a schematic view of side poles attached to the bracing system in accordance with a preferred embodiment of the present invention.

Reference is now made to FIG. 15 illustrating a schematic view of side poles attached to the bracing system in accordance with a preferred embodiment of the present invention. Bracing system 700 that comprises a torso brace 702, a pelvis brace 704, two thigh braces 706, and two shank braces 708, are provided with retractable telescopic side poles 710, acting somewhat as plummets or crutches and prevent an excess lateral or forward/backward bent (indicated by arrows 714) by direct supporting the upper-body brace. Each side pole 710 may be preferably provided with a handle 712 and is supported to bracing system 700 by a spherical joint 716. The side poles may be connected to the controller as well and may be motorized.

An additional stabilizing apparatus may be optionally incorporated into the bracing system, stabilizing shoes as described in Collins, Wisse and Ruina, "A 3-D Passive-Dynamic Walking Robot with Two Legs and Knees," Submitted to publication in the International Journal of Robotics Research, February, 2001; 3-D passive dynamic biped robot. The stabilizing shoes increase the lateral stability and create a side lean sway. Normal gait involves a lateral swing of the body that requires preservation of the center of pressure in the foot area; thus maintains a quasi-static lean stability.

Reference is now made to FIGS. 16a and b illustrating schematic back and side views of a left shoe in accordance with a preferred embodiment of the present invention, respectively. Left shoe 800 is shaped in a way so as to encourage a side lean. As the shoe is wider, the lateral stability is better. In the side view, the rounded shape of shoe 800 is shown. The rounded shape is adapted to ease and soften the step. The bottom of the leg's brace is attached to shoe 800 and a socket 804 is provided in order for the user to insert its own foot.

Algorithm wise, the method of climbing stairs is illustrated as a variation of the gait mode. In this mode, the propelling mechanism is shifted into a low gear, either automatically or manually, and the relevant pattern is used. As in the gait mode, the user dictates the exact pattern parameters, such as step height and depth, by the extent of body tilt and via the MMI. As in the gait mode, a forward step is formed upon a forward-upper-body tilt.

Moving downward can be performed by another algorithm. Reference is now made to FIG. 17 illustrating a descent mode algorithm in accordance with a preferred embodiment of the present invention. Again, the initial position is a stance position 650. The user that wishes to descent stairs, for example, tilts the upper body 652 and similar to the algorithm of the gait mode, the device computes steps parameters 654. The device starts the motors in order to performs a slight forward tilt 656 that produces a forward locked-knee small step (say right, $\theta_{RL}=\theta_{RT}\rightarrow\sim10°$) while folding the other leg 658 ($\theta_{LT}\rightarrow\sim-5°$, $\theta_{LL}\rightarrow\sim-50°$). After the right limb is stabilized on the lower surface 660, the left limb continues the pattern to a stance or to a farther descent 662. As in the gait mode, the hip and knee motors follow predefined patterns supplied by the pattern bank and adjusted to the user movements.

Other modes that were mentioned herein are trainer mode, test mode and learn/adapt mode. In the trainer mode, the gait-locomotor apparatus of the present invention can be used for an active/passive bicycling operation. The user may combine his own muscle force with the propulsion force, where the ratio between the two is set by the user according to the level of disability. In the test mode the controller initiates a self-test algorithm. The user doesn't necessarily have to wear the device during this mode. The self-test may include the following:

Battery check (e.g., short-recovery curve in addition to on-line voltage measurement).

Connections test by transmitting and receiving acknowledgement signals.

Sensors test by activating motors and checking the feedbacks.

Controller self-test.

In the learn/adapt mode, the controller acquires the various gait parameters. This mode is mainly used in the learning period of the user. The various patterns, $\{\Theta_p(n)\}$, that reside in the pattern bank (gait pattern, descent pattern etc.) are being adapted to the user's unique parameters.

In all the above-mentioned patterns, upper body tilts were used in order to initiate reaction of the device. The tilt motion can be more complex and include lateral tilts. The exact tilt vector can be detected by tilt sensors as explained herein above, e.g., one sensor for forward/backward tilts and another for sideward tilts. The tilt vector should exceed some threshold to initiate a step. The parameters of this threshold vector (forward and sideward angles and their time derivatives) are adjusted to fit the individual user's needs.

The gait-locomotor apparatus of the present invention can be combined with a functional electrical stimulation (FES) system. The combination of both features incorporates the advantages of the FES system with the advantages of the gait-locomotor apparatus and contributes to a true muscle-based gait. The introduction of FES in the gait-locomotor apparatus enhances the muscle/gait-training/physiotherapy capability of the device; the user is able to combine his own muscle force with the motorized support of the gait-locomotor apparatus.

Figure 18:
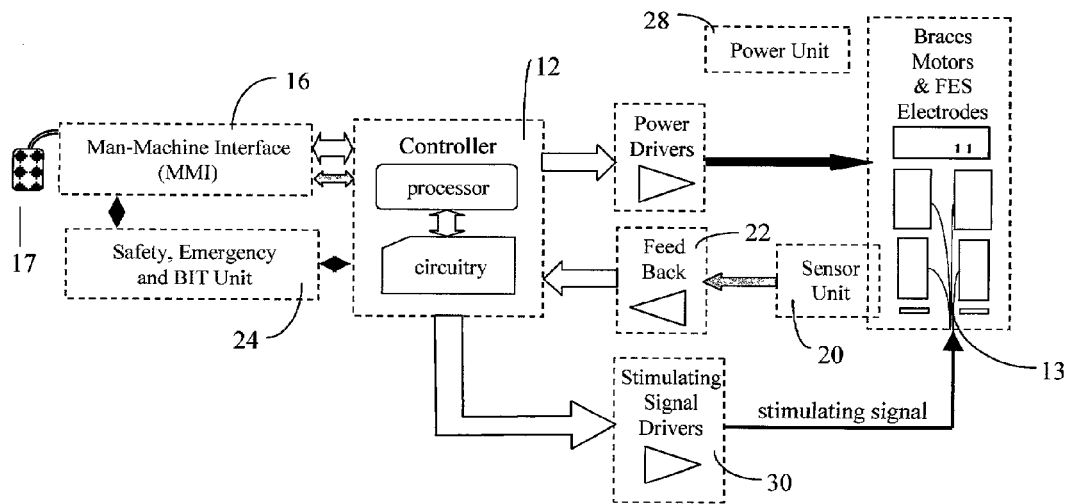
FIG. 18 illustrates a block diagram of a gait-locomotor apparatus in accordance with another preferred embodiment of the present invention, incorporated with a FES system.

Reference is now made to FIG. 18 illustrating a block diagram of a gait-locomotor apparatus in accordance with another preferred embodiment of the present invention, incorporated with a FES system. The gait-locomotor apparatus of the present invention comprises similar features as the gait-locomotor apparatus that was previously discussed. It comprises a brace system 11 that supports parts of the body and electrodes 13 that transfers electrical signals. Brace system 11 contains means of propulsion such as the ones previously shown in FIGS. 2a, 2b and 3.

A relatively small control unit 12 supervises the motion of brace system 11 and the electrical signals that are delivered by electrodes 13. Control unit 12 delivers a command to stimulating signal drivers 30 that generate the stimulating signal that is delivered to the body through electrodes 13. A sensor unit 20 that contains various sensors, monitors parameters and transfers the information to control unit 12 via feedback interfaces 22. The gait-locomotor apparatus further comprises a Man-Machine Interface, MMI 16, through which the person controls modes of operation and parameters of the device. The gait-locomotor apparatus further comprises a power unit 28 that includes portable energy source and related circuitry.

The modes that may be applied in the gait-locomotor apparatus incorporated with FES are:

FES mode: the gait-locomotor apparatus serves as a supportive braking system.

FES-walking mode: the motor system works in parallel to the FES system.

During the FES mode, the gait-locomotor apparatus serves as a controlled-brake orthosis (similar to the patent discloses in U.S. Pat. No. 5,476,441), where the motors are used as a braking system and the bracing system supports the body, reducing the muscles fatigue. A sequence of stimulating signals are applied to the lower limbs in an alternate manner and in accordance with the upper-body tilt; a gait is created by periodically swinging the torso between upright and tilt positions. As in the regular gait mode of the former embodiment, the tilt sensors that are located on the torso sense the periodical tilt motions and synchronize the swap between the lower limbs. Therefore, the need for external command for each step is now redundant. When muscles fatigue is identified by reduce in walking speed, for example, the combined system can automatically switch to the regular gait mode.

Figure 19:
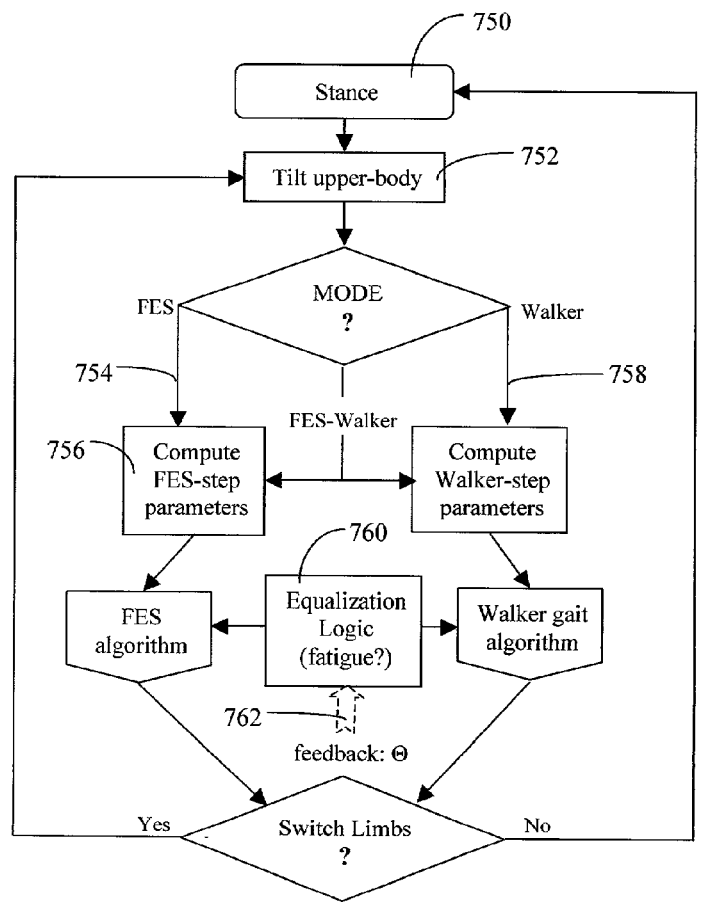
FIG. 19 illustrates a gait mode algorithm in accordance with another preferred embodiment of the present invention, incorporated with FES system.

In the FES-gait-locomotor apparatus mode, the motorized brace system takes part of the gait burden; the muscle force is combined with the motor force. Reference is now made to FIG. 19 illustrating a gait mode algorithm in accordance with another preferred embodiment of the present invention. Again, the initiation is from stance 750 and a tilt of the upper body 752 indicated the desire to walk. Upon selecting the FES-gait-locomotor apparatus mode 754, both gait-restoration methods are computed; the equalization logic 760 assumes, for example, that FES has the priority in actuating the gait 756. Failure in performing the gait pattern, which may be detected by the equalization logic via feedback signals 762, will result in actuation of the gait-locomotor apparatus mode 758, where the extent of the device's support depends on the FES performance. Thus equalization logic 760 resides the algorithm that determines the amount of involvement of each method in the gait process that satisfies the target angles as well as the user choice (made via the MMI).

While several methods of actuating articulations has been described, it will be apparent to those skilled in the art that the method described herein are supplied as an example of preferred embodiments. Thus words like motor, linear motor, air muscle, and the like are directed to any actuator type fitting for the task of actuating the articulations and parts described. It is also apparent that any arrangement providing controlled articulations, is an operative equivalent that falls under the invention, the selection of which is a matter of technical choice of common engineering skills. The motion control hardware and software described may similarly be selected in accordance with technical preference without departing from the invention.

The invention claimed is:

1. A gait-locomotor apparatus for support gait, stance and climb, and transitions between lie-sit-stance positions of a person with a locomotion disability, the apparatus comprising:
   an exoskeleton bracing system comprising jointed support arms for coupling to the trunk of the body and lower limbs of the person;
   propulsion means coupled to the exoskeleton bracing system, for providing relative movement between said segments to parts of the exoskeleton bracing system;
   a plurality of sensors for sensing tilt of the trunk and angular position of parts of exoskeleton bracing system;
   a control unit for receiving information from said plurality of sensors, and for identifying the relative position of parts of the exoskeleton bracing system, the tilt of the person with respect to the ground and gait phases or other phases of modes of operation, a current mode of operation being manually set by the person by an interface into the control unit, processing information in accordance with the current mode of operation and activating and controlling the propulsion system in accordance with a set of predefined movement modes or patterns;
   whereby the apparatus establishes a man-machine interface relation with the person with the locomotion disability, and aids the person in acquiring locomotion as desired.

2. The gait-locomotor apparatus as claimed in claim 1, wherein the exoskeleton bracing system comprises a torso brace and a pelvis brace adapted to fit the trunk of the person, two thigh braces adapted to fit the thighs of the person, and two leg braces adapted to fit the legs and feet of the person.

3. The gait-locomotor apparatus as claimed in claim 1, wherein stabilizing shoes are provided and are attached to the exoskeleton bracing system, said stabilizing shoes are adapted to increase the lateral stability.

4. The gait-locomotor apparatus as claimed in claim 3, wherein said stabilizing shoes are adapted to maintain a side lean.

5. The gait-locomotor apparatus as claimed in claim 3, wherein said stabilizing shoes are provided with a rounded bottom.

6. The gait-locomotor apparatus as claimed in claim 1, wherein said exoskeleton bracing system is provided with two side crutches adapted to provide direct support to the person.

7. The gait-locomotor apparatus as claimed in claim 6, wherein said two side crutches are retractable so as to facilitate height adjustments.

8. The gait-locomotor apparatus as claimed in claim 7, wherein at least one of said two side crutches comprises at least two members that are telescopically connected so as to adjust the length of the side crutch.

9. The gait-locomotor apparatus as claimed in claim 6, wherein each of said two side crutches is provided with a handle that facilitates grasping of the crutches.

10. The gait-locomotor apparatus as claimed in claim 6, wherein said two side crutches are provided with a motorizes system that is adapted to actuate the side crutches and wherein said motorized system is electrically connected to said control unit.

11. The gait-locomotor apparatus as claimed in claim 1, wherein said propulsion system is coupled to articulations between the jointed segments of said exoskeleton bracing system.

12. The gait-locomotor apparatus as claimed in claim 1, wherein said propulsion system comprises linear motors.

13. The gait-locomotor apparatus as claimed in claim 12, wherein two of the motors are adjacent to a hip of the person.

14. The gait-locomotor apparatus as claimed in claim 12, wherein two of the motors are adjacent to the knees of the person.

15. The gait-locomotor apparatus as claimed in claim 12, wherein at least one of the linear motors is provided with a stator provided with a forcer, said stator is attached to one of the jointed support arms, and wherein said forcer is coupled to a lever that is attached to an adjoining support arm.

16. The gait-locomotor apparatus as claimed in claim 15, wherein said lever has a laterally protruding portion, and wherein said forcer is coupled to said portion.

17. The gait-locomotor apparatus as claimed in claim 15, wherein said stator is pivotally connected to the jointed support arm.

18. The gait-locomotor apparatus as claimed in claim 1, wherein said propulsion system comprises a thrust force motor having a linear motor provided with gearing ability, said linear motor is attached to one of the jointed support arms, and wherein a forcer of said linear motor is connected to a belt having two ends, said belt circles about a wheel and is further coupled to a lever attached to an adjoining articulated support arm.

19. The gait-locomotor apparatus as claimed in claim 18, wherein said lever is provided with two opposite lateral protrusions, and wherein each of the two ends of said belt is connected to one of the lateral protrusions of said lever.

20. The gait-locomotor apparatus as claimed in claim 18, wherein said lever is a cogwheel attached in an articulation between jointed support arms.

21. The gait-locomotion apparatus as claimed in claim 1, wherein said propulsion system comprises a thrust force motor in which a linear motor having gearing ability is attached to a jointed support arm between two articulations, and wherein a stator of said linear motor is provided with two adjacent wheels, said stator is provided with a first forcer coupled to a belt, said belt circles about one of the wheels and circles a cogwheel that is attached adjacent to one of the articulations, and wherein said stator is provided with a second forcer coupled to another belt that circles about the other wheel and circles another cogwheel that is attached adjacent to the other articulation.

22. The gait-locomotor apparatus as claimed in claim 1, wherein said propulsion system comprises an air muscle actuator.

23. The gait-locomotor apparatus as claimed in claim 1, wherein said propulsion system comprises a rotary motor.

24. The gait-locomotor apparatus as claimed in claim 23, wherein said rotary motor is positioned in an articulation between jointed support arms of said bracing system.

25. The gait-locomotor apparatus as claimed in claim 24, further comprising a plurality of interacting cogwheels, at least one of the cogwheels is connected by a movable belt to another wheel so as to provide relative movement between the jointed support arms.

26. The gait-locomotor apparatus as claimed in claim 25, wherein said two interacting cogwheels are concentric.

27. The gait-locomotor apparatus as claimed in claim 1, wherein at least one of the sensors is a tilt sensor.

28. The gait-locomotor apparatus as claimed in claim 27, wherein a goniometer is attached to articulations between jointed support arms of said bracing system in order to measure the articulation angle.

29. The gait-locomotor apparatus as claimed in claim 1, wherein at least one of the sensors is an acceleration sensor.

30. The gait-locomotor apparatus as claimed in claim 29, wherein at least one of the sensors is an accelerometer.

31. The gait-locomotor apparatus as claimed in claim 1, wherein said information comprises angles of articulation between jointed support arms of said bracing system.

32. The gait-locomotor apparatus as claimed in claim 1, wherein said information comprises accelerations of body parts of the person.

33. The gait-locomotor apparatus as claimed in claim 1, wherein said information comprises angular velocities.

34. The gait-locomotor apparatus as claimed in claim 1, wherein a processor is incorporated in said control unit, said processor adapted to execute motion control algorithms.

35. The gait-locomotor apparatus as claimed in claim 34, wherein said algorithms comprises commands dictating the angles between the jointed support arms and the position of the jointed support arms so as to perform predetermined modes of operation on said bracing system.

36. The gait-locomotor apparatus as claimed in claim 35, wherein said modes of operation are selected from the group consisting of standing mode, gait mode, climbing mode, descending mode, lie-sit transition mode, sit-stance transition mode, stance-gait transition mode, training mode, learning mode or a combination thereof.

37. The gait-locomotor apparatus as claimed in claim 35, wherein at least one of said modes of operation is initiated by exceeding a threshold value in the angular position of at least one of the jointed support arms.

38. The gait-locomotor apparatus as claimed in claims 36, wherein at least one of said modes of operation is initiated by receiving a signal monitored by at least one of said sensors, said signal indicating that a threshold value has been exceeded in the tilt angle of the torso of the person.

39. The gait-locomotor apparatus as claimed in claim 1, wherein said control unit is communicating with said propulsion system through power drivers.

40. The gait-locomotor apparatus as claimed in claim 1, wherein said control unit is communicating with a man-machine interface adapted to receive commands from the person.

41. The gait-locomotor apparatus as claimed in claim 1, wherein at least one of the sensors is communicating with said control unit through feedback interfaces.

42. The gait-locomotor apparatus as claimed in claim 1, wherein said gait-locomotor apparatus further comprises a safety unit and a built-in test unit.

43. The gait-locomotor apparatus as claimed in claim 42, wherein said safety unit is communicating with said control unit.

44. The gait-locomotor apparatus as claimed in claim 42, wherein said safety unit is communicating with at least one of the sensors.

45. The gait-locomotor apparatus as claimed in claim 1, wherein said gait-locomotor apparatus further comprises a power unit.

46. The gait-locomotor apparatus as claimed in claim 1, wherein at least one of the sensors provides a warning signal.

47. The gait-locomotor apparatus as claimed in claim 46, wherein the warning signal indicates the power status of the gait-locomotor apparatus.

48. The gait-locomotor apparatus as claimed in claim 46, wherein a warning signal indicates currents in said propulsion system.

49. The gait-locomotor apparatus as claimed in claim 1, wherein said gait-locomotor apparatus further comprises at least one temperature sensor.

50. The gait-locomotor apparatus as claimed in claim 49, wherein said gait-locomotor apparatus further comprises overheat protection.

51. The gait-locomotor apparatus as claimed in claim 50, wherein said temperature is monitored in said propulsion system.

52. The gait-locomotor apparatus as claimed in claim 50, wherein said temperature is monitored in said control unit.

53. The gait-locomotor apparatus as claimed in claim 1, wherein said gait-locomotor apparatus further comprises functional electrical stimulation (FES) means.

54. The gait-locomotor apparatus as claimed in claim 53, wherein said gait-locomotor apparatus further comprises FES electrodes, said electrodes are electrically communicating with a signal generator.

55. The gait-locomotor apparatus as claimed in claim 54, wherein said signal generator is communicating with said control unit.

56. The gait-locomotor apparatus as claimed in claim 54, wherein said control unit further comprises commands dictating the electrical signal that is transferred by the FES electrodes.

57. The gait-locomotor apparatus as claimed in claim 53, wherein said control unit further comprises command that activate the FES means.

58. A gait-restoration method for facilitating gait, stance and climb, and transitions between lie-sit-stance positions of a person with a locomotion disability, the method comprising the steps of:
  providing a gait-locomotor apparatus comprising:
    an exoskeleton bracing system, comprising jointed support arms for coupling to the trunk of the body and lower limbs of the person;

a propulsion system coupled to the exoskeleton bracing system for providing relative movement to parts of the exoskeleton bracing system;

a plurality of sensors for sensing tilt of the trunk and angular position of parts of the exoskeleton bracing system;

a control unit having an algorithm for accomplishing:

receiving information from said plurality of sensors;

identifying the relative position of parts of the exoskeleton bracing system;

identifying tilt and gait phases;

identifying a current mode of operation being manually set by the person via an interface into the control unit;

processing the information in accordance with the current mode of operation; and, activating and controlling the propulsion system in accordance with a set of predefined movement modes or patterns;

setting a desired operation mode;

determining specific movement mode or pattern from the set of predefined movement modes or patterns, upon sensing a tilt of the person, the angle of the tilt and at least a first derivative of the tilt angle; and actuating the propulsion system in accordance with the set of predefined movement modes or patterns.

59. The method of claim 58, wherein the algorithm includes a gait algorithm comprising the following steps:

detecting an upper body tilt of the person, determining the angle of the tilt and at least a first derivative of the tilt angle;

computing parameters for a gait pattern, selected from the set of predefined movement modes or patterns;

initialing a forward step of a first leg of the person by actuating the propulsion system;

placing the foot of the first leg on the ground;

straightening the knee of first leg;

determining when the person reaches an upright position;

if another tilt is sensed repeating the above steps replacing the operations performed by the first leg with similar operations to be preformed by the second leg.

60. The method of claim 59 wherein a stairs-climbing algorithm is incorporated.

61. The method of claim 60, wherein the stairs-climbing algorithm is a climbing-up algorithm, comprising:

detecting an upper body tilt of the person, determining the angle of the tilt and at least a first derivative of the tilt angle;

computing parameters for a stairs-climbing pattern, selected from the set of predefined movement modes or patterns;

initiating a forward step of a first leg of the person by actuating the propulsion system, whereby the foot of the first leg is raised;

placing down the foot of the first leg;

straightening the knee of first leg;

determining that the person have reached an upright position;

if another tilt is sensed, repeating the above steps replacing the operations performed by the first leg with similar operations to be preformed by the second leg.

62. The method of claim 60, wherein the stairs-climbing algorithm is a climbing-down algorithm, comprising:

detecting an upper body tilt of the person, determining the tilt angle and at least a first derivative of the tilt angle;

computing parameters for a stairs-climbing pattern, selected from the set of predefined movement modes or patterns;

initiating a forward step of a first leg of the person while maintaining a the first leg in a straightened posture, by actuating the propulsion system, whereby the foot of the first leg is raised, while simultaneously folding the knee of the second leg;

placing down the foot of the first leg;

determining when the person reaches an upright position;

if another tilt is sensed repeating the above steps replacing the operations performed by the first leg with similar operations to be preformed by the second leg.

63. The method of claim 58 wherein a turn algorithm is incorporated comprising:

sensing an body throwing movement in a certain turn direction;

using a first leg of the person as an axis for the turn, forwarding the second leg across in the turn direction.

64. The method of claim 58, wherein a transition algorithm between a lie position, a sit position, and a stance position is incorporated.

* * * * *